(12) United States Patent
Cho

(10) Patent No.: US 8,942,347 B2
(45) Date of Patent: *Jan. 27, 2015

(54) X-RAY IMAGING APPARATUS AND METHOD FOR CONTROLLING THE SAME

(71) Applicant: Samsung Electronics Co., Ltd., Suwon-si (KR)

(72) Inventor: Min Kook Cho, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/711,887

(22) Filed: Dec. 12, 2012

(65) Prior Publication Data

US 2013/0121465 A1    May 16, 2013

Related U.S. Application Data

(63) Continuation of application No. 13/652,991, filed on Oct. 16, 2012.

(30) Foreign Application Priority Data

Oct. 21, 2011  (KR) .................. 10-2011-0108197

(51) Int. Cl.
  *G01N 23/04*  (2006.01)
  *A61B 6/00*  (2006.01)

(52) U.S. Cl.
  CPC .............. *A61B 6/463* (2013.01); *A61B 6/482* (2013.01); *A61B 6/505* (2013.01); *A61B 6/5241* (2013.01)
  USPC ........................................ 378/62; 378/98.12

(58) Field of Classification Search
  USPC .............. 378/62, 98.11, 98.12; 382/128–132
  See application file for complete search history.

(56) References Cited

U.S. PATENT DOCUMENTS

| 6,683,934 B1 | 1/2004 | Zhao et al. | |
| 2006/0109949 A1* | 5/2006 | Tkaczyk et al. | 378/4 |
| 2009/0096807 A1* | 4/2009 | Silverstein et al. | 345/593 |
| 2009/0279761 A1 | 11/2009 | Fei et al. | |

FOREIGN PATENT DOCUMENTS

| EP | 2 548 510 A1 | 1/2013 |
| JP | 2004-609 A | 1/2004 |
| JP | 2004-147863 A | 5/2004 |

(Continued)

OTHER PUBLICATIONS

L.A. Lehmann, et al., "Generalized image combinations in dual KVP digital radiography", Med. Phys. Sep.-Oct. 1981, pp. 659-667.

(Continued)

*Primary Examiner* — Courtney Thomas
(74) *Attorney, Agent, or Firm* — Sughrue Mion, PLLC

(57) ABSTRACT

The X-ray imaging apparatus includes an X-ray generator to generate X-rays having at least two different energy levels and irradiate the X-rays onto a subject, a detector to detect the X-rays irradiated by the X-ray generator and transmitted through the subject, and a device to obtain images from the X-rays detected by the detector, to obtain bone image information and soft tissue image information of the subject, based on the obtained X-ray images, and to produce one image including the bone image information and the soft tissue image information.

42 Claims, 27 Drawing Sheets

(56) References Cited

FOREIGN PATENT DOCUMENTS

| | | |
|---|---|---|
| JP | 2006-68457 A | 3/2006 |
| JP | 2006-68529 A | 3/2006 |

OTHER PUBLICATIONS http.//www.upstatc.cdu/radiology/education/rsna/radioaraphy/dual/. "Dual Energy Radiography Acquisition and Processing", Radiology, last retrieved Jan. 30, 2013, pp. 1-7, XP002690984.

S. Kubilay Pakin et al., "Clustering approach to bone and soft tissue segmentation of digital radiographic images of extremities", Journal of Electronic Imaging, Jan. 2003, vol. 12(1), pp. 40-49.

Hologic, "Our DXA Technology", "Skeletal Health," http://www.hologic.com/ja/skeletal-health/overview/dxa-technology/; last retrieved Aug. 1, 2014; 4 pages.

ITN (Imaging Technology News), "Hologic Discovery DXA Offers Advanced Body Composition Assessment", http://www.itnonline.com/arlicle/hologic-discovery-dxa-offers-advanced-body-composition-assessment/; last retrieved Aug. 1, 2014; 1 page.

* cited by examiner

X-RAY IMAGING APPARATUS AND METHOD FOR CONTROLLING THE SAME

CROSS-REFERENCE TO RELATED APPLICATION

This application is a continuation of U.S. application Ser. No. 13/652,991 filed Oct. 16, 2012, which claims priority from Korean Patent Application No. 10-2011-0108197, filed Oct. 21, 2011 in the Korean Intellectual Property Office, the disclosures of which are incorporated herein by reference in their entireties.

BACKGROUND

1. Field

Apparatuses and methods consistent with exemplary embodiments relate to obtaining an X-ray image of bones and soft tissues of a subject using a plurality of X-rays having different energy levels.

2. Description of the Related Art

An X-ray imaging apparatus irradiates an X-ray onto a subject, analyzes the X-ray passing through the subject and, thereby, an inner structure of the subject may be observed. Since transmission of X-rays is varied depending on the structure of the subject, the inner structure of the subject can be imaged using an attenuation coefficient expressed as a numeral value of this variation.

Recently, methods for obtaining an X-ray image by irradiating an X-ray having different energy levels, instead of an X-ray with a single energy, have been developed and a variety of research associated therewith is underway.

According to one or more of these methods, an energy X-ray imaging apparatus sequentially irradiates an X-ray with a first energy and an X-ray with a second energy onto a subject to obtain a plurality of transmission images and thereby to obtain a clear image in which bones and soft tissue of the subject are separated using the images. However, such X-ray imaging apparatus independently outputs individual images of bones and soft tissues, thus being disadvantageous in that it is difficult to confirm the geometric relation between bones and soft tissues and observation of a plurality of images is inconvenient.

SUMMARY

Exemplary embodiments may address at least the above problems and/or disadvantages and other disadvantages not described above. Also, exemplary embodiments are not required to overcome the disadvantages described above, and an exemplary embodiment may not overcome any of the problems described above.

According to an aspect of an exemplary embodiment, there is provided an X-ray imaging apparatus and a method for controlling the same for obtaining an X-ray image of bones and soft tissues using X-rays having different levels of energy, wherein one image of bones and soft tissues is output to enable a user to confirm conditions of a subject through one image and, at the same time, to easily confirm a relation between bones and soft tissues.

According to another aspect of an exemplary embodiment, there is provided an X-ray imaging apparatus and a method for controlling the same wherein one image of bones and soft tissues is output and the bones and soft tissues are represented by different colors or brightness to enable a user to easily distinguish the bones from the soft tissues.

In accordance with an aspect of an exemplary embodiment, an X-ray imaging apparatus includes: an X-ray generator to generate an X-ray and irradiate the X-ray to a subject; a detector to detect the X-ray irradiated by the X-ray generator and transmitted through the subject; and a host device to obtain an image from the X-ray detected by the detector, to obtain bone image information and soft tissue image information of the subject, based on the obtained X-ray image, and to produce and output one image including the bone image information and soft tissue image information.

The host device may include: an image acquirer to produce one image including all of the bone image information and soft tissue image information; and an image output to output the image produced by the image generator.

The image generator may make brightness of a region of bone different from brightness a region of soft tissue in the one image.

The host device may further include: a color mapper to separately map the obtained image information onto different color channels among a plurality of color channels.

The image generator may produce one image including all of the obtained image information mapped onto the different color channels.

The host device may further include: an input device to receive selection of at least one of bone and soft tissue from a user, wherein the image generator further produces one image including image information of the bone or soft tissue selected via the input device.

The host device may further include an input device to receive selection of at least one of bone and soft tissue by a user, wherein the image generator makes brightness of a region of bone or soft tissue selected via the input device in the one image different from brightness of a region of a non-selected bone or soft tissue.

The host device may further include: an input device to receive selection of one of bone image information and soft tissue image information mapped onto different color channels by a user, wherein the image generator further produces one image including only the image information selected via the input device.

The host device may further include: an input device to receive selection of one from image information mapped onto different color channels by a user, wherein the image generator further produces one image including all of the selected image information and non-selected image information, wherein the image generator makes brightness of a region of bone be different from brightness a region of soft tissue in the one image.

The color mapping performed by the color mapper may be set or varied by the user.

The host device may further include: an input device to receive instruction associated with variation in weight of bone and soft tissue in the one image from a user, wherein the image generator controls the weight of bone and soft tissue in one image output from the image generator depending on the input instruction.

In accordance with an aspect of an exemplary embodiment, a method for controlling an X-ray imaging apparatus includes: generating an X-ray and irradiating the same to a subject; detecting the X-ray transmitted into the subject; obtaining an X-ray image from the detected X-ray; obtaining image information of bone and soft tissue of the subject, based on the obtained X-ray image; and producing and outputting one image including all of the obtained image information.

The producing one image may further include making brightness of a region of bone be different from brightness a region of soft tissue in the one image.

The method may further include: separately mapping the obtained respective image information onto different color channels among a plurality of color channels.

The one image may be an image including all of color channels mapped with the obtained image information.

The method may further include: receiving selection of at least one of bone and soft tissue by a user; and producing one image including only image information of the selected bone or soft tissue.

The method may further include: receiving selection of one from color channels mapped with the obtained image information by a user; and producing one image including only the selected color channel.

The method may further include: receiving selection of at least one from bones and soft tissues by a user, wherein the producing one image further includes making a region of the selected bones or soft tissue image information brighter than a region of the non-selected bones or soft tissue image information in the one image.

The method may further include: receiving selection of one from color channels mapped with the obtained image information by a user, wherein the producing one image further includes making a region of the selected color channel brighter than a region of the non-selected color channel in the one image.

The method may further include: receiving instruction associated with variation in weight of bones and soft tissues in the one image from a user; and controlling a weight of bone and soft tissue in the output image, depending on the input instruction.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
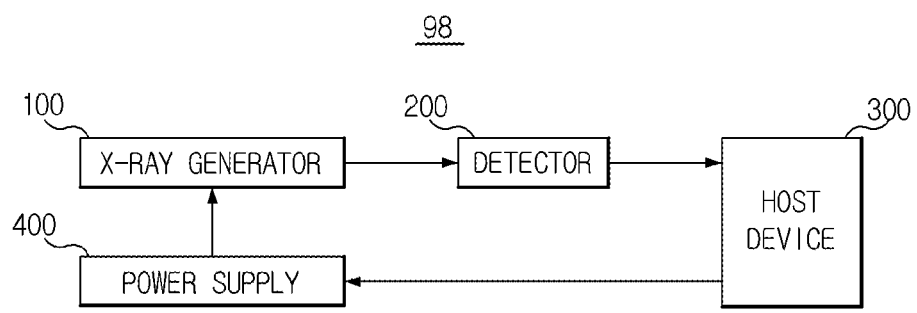
FIG. 1 is a block diagram illustrating an X-ray imaging apparatus according to an exemplary embodiment.

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

Hereinafter, an X-ray imaging apparatus according to an exemplary embodiment will be described with reference to the accompanying drawings.

FIG. 1 is a block diagram illustrating an X-ray imaging apparatus according to an exemplary embodiment.

Referring to FIG. 1, the X-ray imaging apparatus 98 according to an exemplary embodiment includes an X-ray generator 100 to generate X-rays and irradiate the X-rays to a subject, a power supply 400 to supply power to the X-ray generator 100, a detector 200 to detect the X-rays which are generated by the X-ray generator 100 and transmitted through the subject, and a host device 300 to obtain images detected by the detector 200, to obtain image information of bones and soft tissues of the subject, based on the obtained X-ray images, and to produce and output one image including a plurality of pieces of image information.

The X-ray generator 100 receives power from the power supply 400, generates an X-ray and irradiates the X-ray to a subject. The energy intensity and amount of irradiated X-rays depend on the intensity and timing of the power supplied from the power supply 400.

The power supply 400 supplies power having a predetermined voltage to the X-ray generator 100 to generate an X-ray and the intensity of power supplied from the power supply 400 is controlled by the host device 300.

The detector 200 detects X-rays transmitted through the subject. The X-rays, which are irradiated by the X-ray generator 100, are transmitted through the subject, and, at the same time, are attenuated. The transmission of X-ray depends on the structure constituting a region to which the X-ray is irradiated and the amount of transmitted X-ray depends on the position at which the X-ray is irradiated.

The structures having different X-ray transmission may be classified into soft tissues such as fat, muscle and blood, tissues containing a great amount of calcium such as bones and teeth, and gases. Accordingly, the amount of transmitted X-ray depends on the area of the subject, such as bone, soft tissue and gas or fat tissue, to which the X-ray is irradiated.

The detector 200 includes an image intensifier and a CCD camera and detects an X-ray transmitted through the subject, intensifies an image through the image intensifier, converts the image into an electrical signal and transfers the electrical signal to the host device 300.

The host device 300 obtains images of respective X-rays having different energies through image-processing, based on the transferred electrical signal, and obtains image information associated with bones and soft tissues of the subject from the obtained image. The host device 300 produces and outputs an image including image information of the bones and soft tissues.

As described above, according to an exemplary embodiment, X-ray images of X-rays having different energies are obtained and image information of bones and soft tissues is obtained using the same. The methods for obtaining X-ray images of X-ray having different energies may include a first method in which a separate irradiation is used, and a second method including irradiation of X-ray, detection and separation of X-ray having a desired energy level.

In the first method, the X-ray generator 100 generates X-rays having different energy levels and irradiates the same to a subject, the detector 200 detects the X-rays from the subject and sends the electrical data to the host device 300, and the host device 300 obtains an image of each X-ray through image-processing.

In the second method, the X-ray generator 100 irradiates an X-ray having a predetermined level of energy once, and a photon counting detector (PCD) embodied in the detector 200 separates the X-rays according to energy levels.

Specifically, when X-ray transmitted through the subject reaches a photodiode region of the PCD, electrons that stay in a valence band receive a photon energy of X-ray and are excited to a conduction band over a band gap energy gap. Such excitation causes production of a great amount of electron-hole pairs even in a depletion region. The electron-hole pairs are moved by an electric field and a current thus flows. When the level of this current is detected, level data of X-ray that is transmitted through the subject and reaches a pixel can be obtained and an image can be obtained by collecting the data of respective pixels.

The PCD converts current produced according to flow of electron-hole generated whenever a photon corresponding to the energy of X-ray is incident, into a voltage signal and intensifies the same, and inputs the same to a comparator. The comparator compares the intensified voltage signal with a reference voltage to output pulses and a counter counts pulses output from the comparator per unit time to measure a level of X-ray.

In an exemplary embodiment, image information of bones and soft tissues is obtained from a plurality of images of multiple energy X-rays and one image including image information of the bones and soft tissues is produced, by using, for example, one of the described-above the first method or the second method to obtain a plurality of X-ray images.

In exemplary embodiments described below, the first method is described for convenience of description; that is, a method for obtaining a plurality of X-ray images by irradiating X-ray two or more times.

Figure 2:
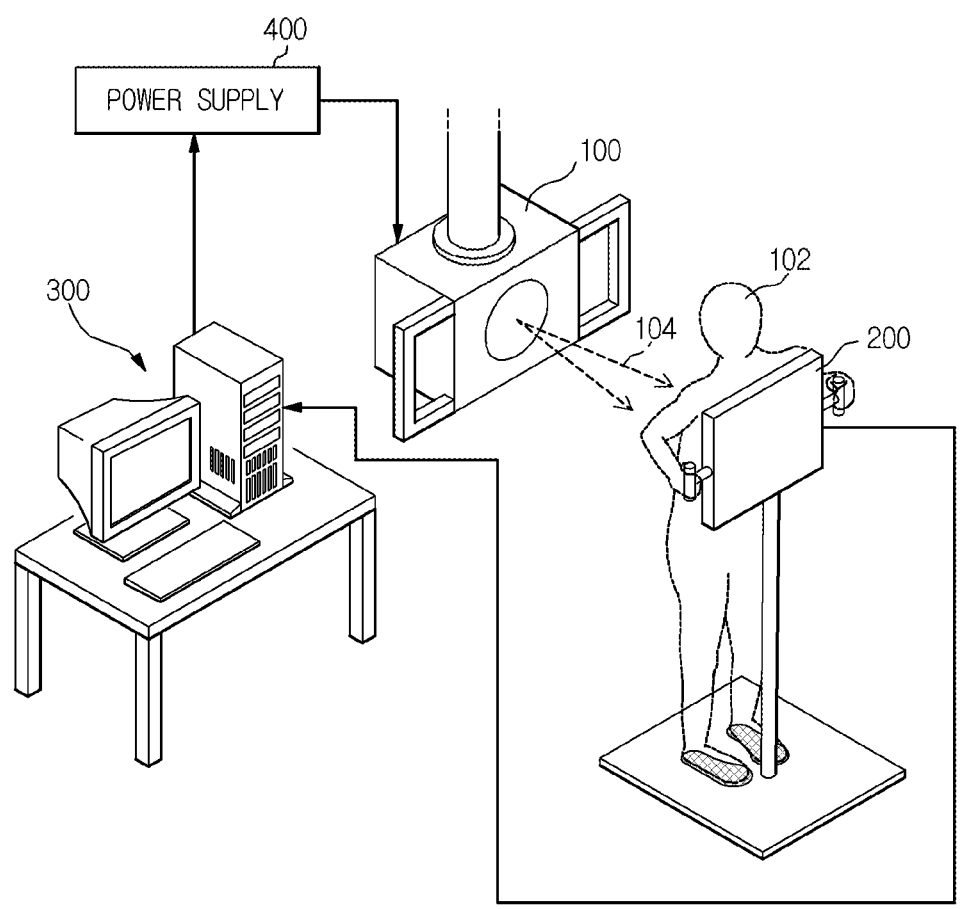
FIG. 2 is a view illustrating an overall configuration of an X-ray imaging apparatus according to an exemplary embodiment.

FIG. 2 is a view illustrating the overall structure of an X-ray imaging apparatus according to an exemplary embodiment.

Referring to FIG. 2, an X-ray generator 100 is mounted such that it faces a detector 200 spaced from the X-ray generator 100 by a predetermined distance. A power supply 400 is connected to the X-ray generator 100 to supply voltage and current, so that the X-ray generator 100 generates X-rays.

The power supply 400 is controlled by the host device 300 and supplies a predetermined voltage and current to the X-ray generator 100 in order to generate an X-ray in a test site of the subject 102.

In a case in which a human is the subject, the human assumes a posture suitable for the site to be imaged in front of the detector 200. For example, in a case in which a breast is imaged, the breast of the human is brought into contact with the detector 200 and the back of the human faces the X-ray generator 100. The detector 200 detects an X-ray 104 that is irradiated by the X-ray generator 100 and is transmitted through the subject, converts the X-ray into an electrical signal and transfers the same to the host device 300.

The host device 300 is connected to the detector 200 and the power supply 400, transfers control signals that control voltage and current to the power supply 400, and obtains an X-ray image of each X-ray from the detector 200, based on the transmitted X-ray signal. In addition, the host device 300 obtains image information of bone and soft tissue using the difference in attenuation coefficient between the bone and soft tissue generated in each X-ray image, and outputs an image including the image information on an image output device, thus enabling a medical professional to detect whether the subject has any abnormality and/or suffers from a disease.

The view illustrating the overall structure of the apparatus of FIG. 2 is provided for description of an exemplary embodiment. The X-ray imaging may be carried out in a state in which the subject lies or sits and the position of each constituent component is not limited to that shown in FIG. 2 so long as the apparatus includes components performing the desired functions.

Hereinafter, an operation of the host device 300 of the X-ray imaging apparatus according to an exemplary embodiment described with reference to FIG. 1 will be described in detail.

Figure 3:
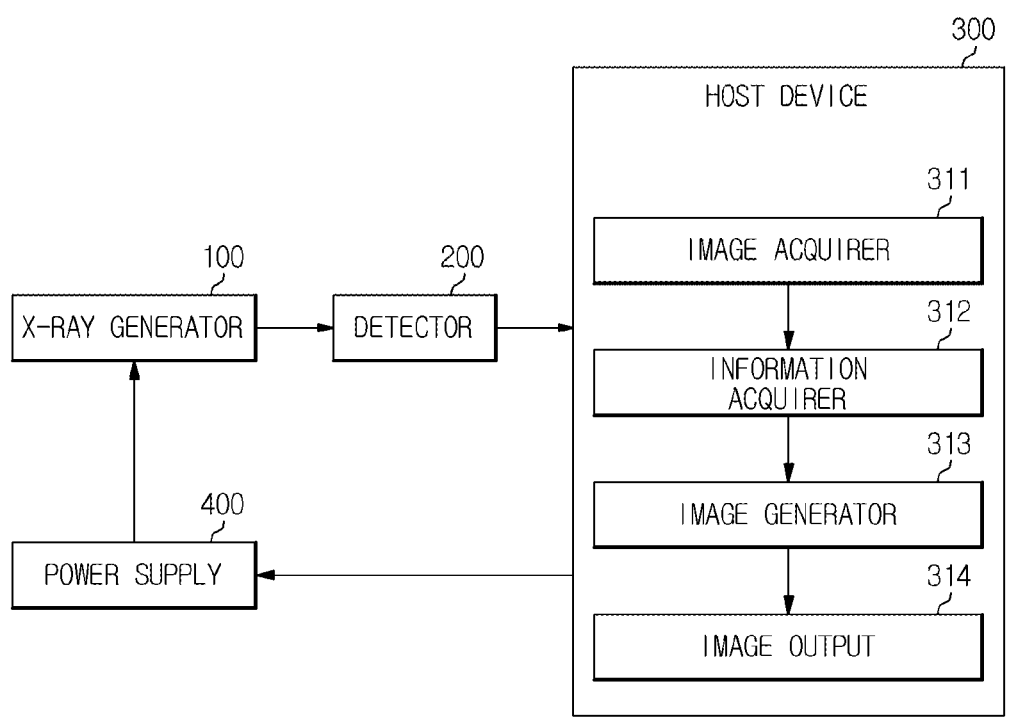
FIG. 3 is a detailed block diagram illustrating a host device of an X-ray imaging apparatus according to an exemplary embodiment.

FIG. 3 is a detailed block diagram illustrating a host device 300 of the X-ray imaging apparatus according to the exemplary embodiment described with reference to FIG. 1.

Referring to FIG. 3, in the X-ray imaging apparatus according to an exemplary embodiment, the host device 300 includes an image acquirer 311 to obtain an X-ray image through image-processing of an electrical signal transferred from the detector 200, an information acquirer 312 to obtain image information of bones and soft tissues, based on the obtained X-ray image and difference in attenuation between bones and soft tissues, an image generator 313 to produce an image including all of the obtained image information, and an image output 314 to output the produced image.

As discussed above, when power is supplied from the power supply 400 to the X-ray generator 100, the X-ray generator 100 generates X-ray having an energy corresponding to the supplied power, and the detector 200 detects the X-ray that is irradiated by the X-ray generator 100 and transmitted through the subject, and transfers the X-ray data, such as electrical data, to the host device 300.

The X-ray generator 100 generates energy having different levels depending on the supplied power. In an exemplary embodiment, the number of energy levels is not limited, but X-rays having a first energy and a second energy having different levels are sequentially irradiated as described in detail below. The sequential irradiation refers to the irradiation with the X-rays having different energy levels which are not simultaneously irradiated onto the subject, and the irradiation order of the first energy level and the second energy level is not limited thereto.

The image acquirer 311 obtains an X-ray image of the first energy and an X-ray image of the second energy through image-processing of an X-ray signal or electrical signal transferred from the detector 200. The image-processing method performed by the image acquirer 311 may be one of the known image-processing methods for producing the X-ray image.

Figure 4A:
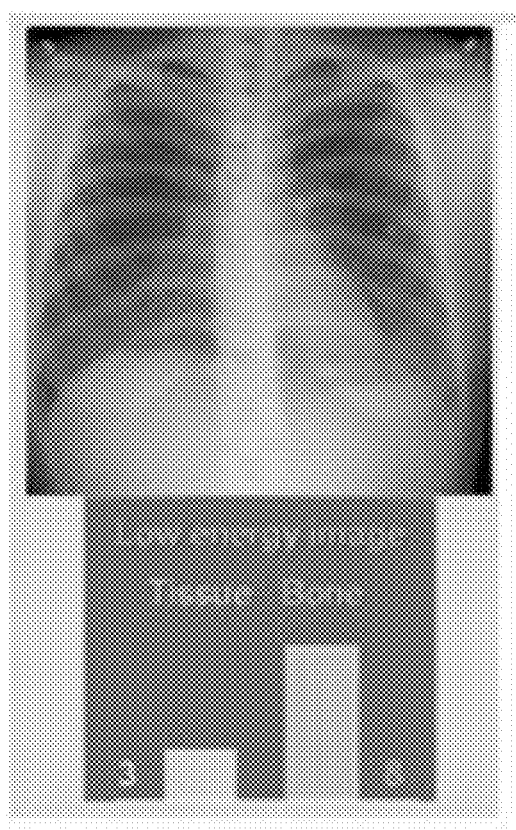
FIGS. 4A and 4B are X-ray images obtained from an X-ray imaging apparatus according to an exemplary embodiment.
Figure 4B:
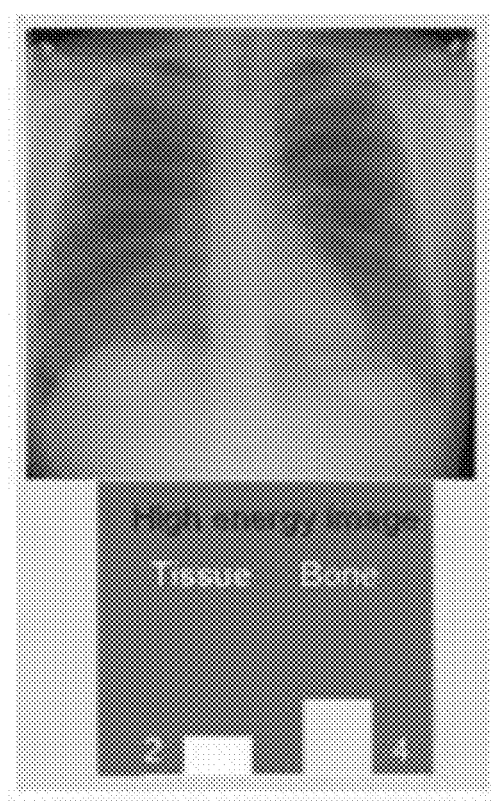

FIGS. 4A and 4B are X-ray images obtained by the image acquirer 311. FIG. 4A is an X-ray image of a first energy having a relatively low energy and FIG. 4B is an X-ray image of a second energy having a relatively high energy. Referring to FIGS. 4A and 4B, attenuation properties of bones and soft tissues may be varied depending on energy intensity of the X-ray. In the information acquirer described below, image information of bones and image information of soft tissues are obtained using these properties.

The information acquirer 312 obtains image information of bones and soft tissues from the X-ray image of the first energy and the X-ray image of the second energy obtained through the image acquirer 311, using difference in attenuation properties between bones and soft tissues. Hereinafter, a process for obtaining image information of bones and soft tissues will be described in detail.

As described above, transmissivity or attenuation factor is varied depending on the material through which the X-rays are transmitted. An X-ray image is an image showing an inner structure of the subject using this property. The attenuation factor of the X-ray is numerically expressed as an attenuation coefficient. The attenuation coefficient shows a relation between intensity (Io) of the X-ray incident onto a subject and a resultant intensity (I) of the X-ray transmitted through the thickness (t) of the subject and is represented by the following Equation 1.

$$I = I_o * \exp(-\mu t) \qquad \text{[Equation 1]}$$

wherein μ represents an attenuation coefficient.

Accordingly, as the attenuation coefficient increases, an intensity of transmitted X-ray decreases. Thus, as the attenuation coefficient increases, transmissivity of the X-ray through a subject decreases, and, as the attenuation coefficient decreases, the transmissivity of the X-ray through a subject increases.

Figure 5:
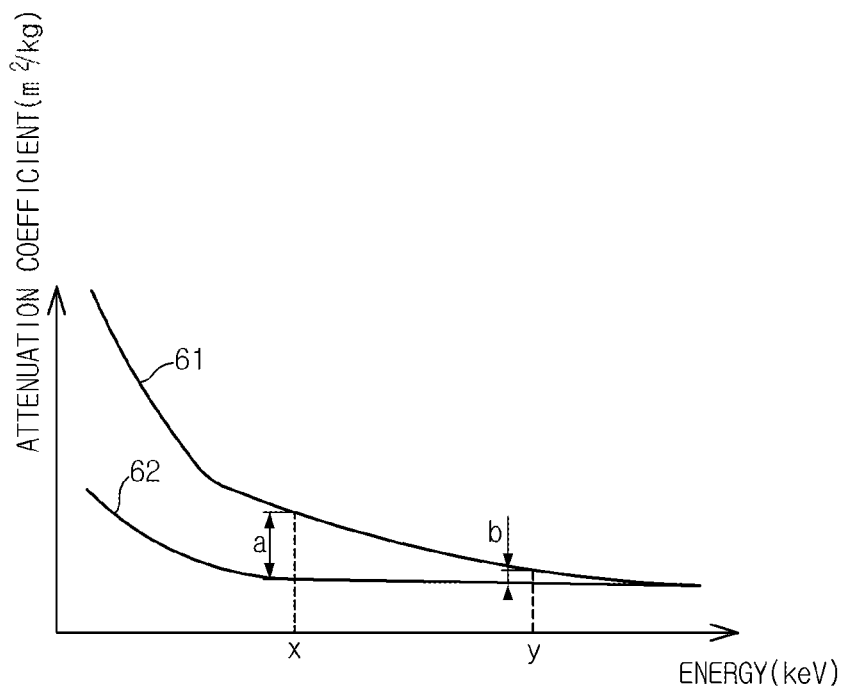
FIG. 5 is a graph showing X-ray attenuation coefficients of bones and soft tissues.

FIG. 5 is a graph showing curves 61 and 62 of the attenuation coefficients of the bones and soft tissues, respectively. Referring to the graph, as the energy of X-ray increases, the values of the attenuation coefficients decrease. This means that, as energy of X-ray increases, X-ray is more effectively transmitted through the subject. In addition, referring to the graph of FIG. 5, a curve 61 showing an attenuation coefficient of the bones is disposed above a curve 62 showing an attenuation coefficient of the soft tissues. This means that a transmissivity of the X-ray in the soft tissue is higher than a transmissivity of the X-ray in the bone.

As can be seen from the graph of FIG. 5, a difference in two attenuation coefficients is varied depending on the intensity of energy. The difference a in the attenuation coefficients between the bone and the soft tissue at the point at which the energy of X-ray corresponds to x keV is higher than the difference b in attenuation coefficient between the bone and the soft tissue at the point at which the energy of the X-ray corresponds to y keV. That is, as the energy of X-ray decreases, the difference in the attenuation coefficients between the bone and the soft tissue increases.

In an exemplary embodiment, a dual energy subtraction method enabling the information acquirer 312 to obtain image information using the difference in attenuation properties between the bone and the soft tissue may be used. The dual energy subtraction method is a method for extracting image information clearly expressing the desired site of bones and soft tissues by representing images obtained at a high energy and a low energy by a logarithm and obtaining the difference between two images by using an applicable weight.

$I_L$ and $I_H$ of the Equations 2 and 3 represent image information expressed as a logarithmic value of image information obtained from an X-ray with a low energy and of image information obtained from an X-ray with a high energy, respectively, and $w_b$ and $w_s$, representing a weight can be expressed by the Equations 4 and 5, respectively.

$$I_{bone} = I_L w_b - I_H \qquad \text{[Equation 2]}$$

$$I_{soft} = I_H - w_s I_L \qquad \text{[Equation 3]}$$

$$w_b = \mu_{bone}(E_H)/\mu_{bone}(E_L) \qquad \text{[Equation 4]}$$

$$w_s = \mu_{soft}(E_H)/\mu_{soft}(E_L) \qquad \text{[Equation 5]}$$

wherein $\mu_{bone}(E_H)$ represents an attenuation coefficient of the bone at a high energy, $\mu_{bone}(E_L)$ represents an attenuation coefficient of the bone at a low energy, $\mu_{soft}(E_H)$ represents an attenuation coefficient of the soft tissue at a high energy, and $\mu_{soft}(E_L)$ represents an attenuation coefficient of the soft tissue at a low energy.

A weight is obtained using Equations 4 and 5 and is substituted in Equations 2 and 3 to obtain an image information $I_{bone}$ of a bone and an image information $I_{soft}$ of the soft tissue, respectively.

The image information of the bone is image information in which afterimage of the soft tissue is removed and the bone is thus clearly expressed. The image information of the soft tissue is image information in which afterimage of the bone is removed and the soft tissue is thus clearly expressed.

The dual energy subtraction method is provided only as an example of a method for obtaining an X-ray image of double energy and an exemplary embodiment is not limited to the aforementioned method.

The image generator 313 produces one image including all of image information of bones and image information of soft tissues obtained from the information acquirer, and outputs the image through the image output, to enable a user or tester to observe the condition of bones and soft tissues from the one image.

The configuration of the image output 314 is not limited so long as it is capable of outputting and displaying an X-ray image.

Figure 6A:
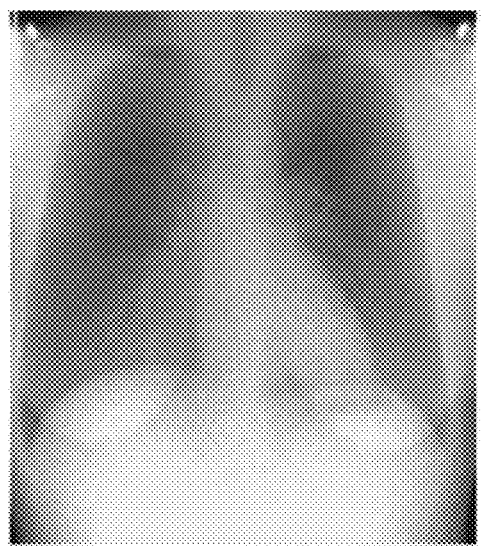
FIGS. 6A and 6B show X-ray images output from a dual energy X-ray imaging apparatus of the related art.
Figure 6B:
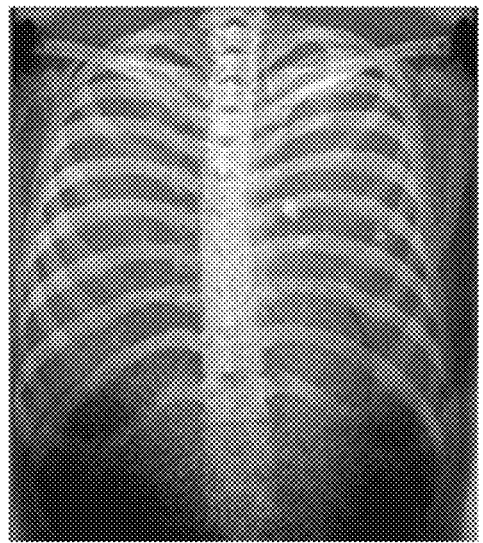
Figure 7:
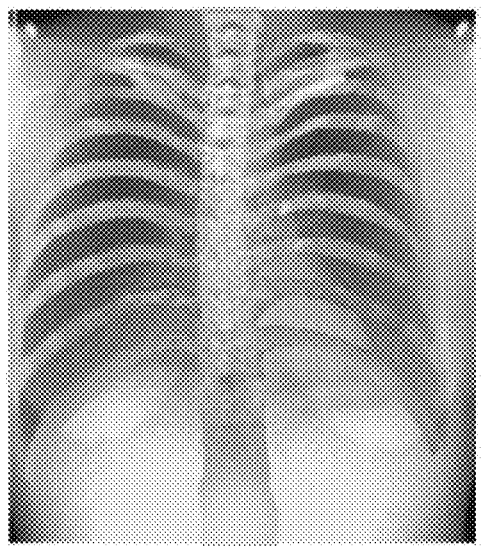
FIG. 7 is an example of an X-ray image output from the X-ray imaging apparatus according to an exemplary embodiment.

FIGS. 6A and 6B illustrate X-ray images output from a dual energy X-ray imaging apparatus of the related art, and FIG. 7 illustrates an X-ray image output from the image output of an X-ray imaging apparatus according to an exemplary embodiment.

Referring to FIGS. 6A and 6B, in the related art, an X-ray image showing a bone and an X-ray image showing a soft tissue are independently produced and output. A user needs to separately analyze both the X-ray image showing a bone and the X-ray image showing a soft tissue in order to observe the condition of the subject and cannot easily analyze relation between bone and soft tissue.

As shown in FIG. 7, the X-ray imaging apparatus according to an exemplary embodiment produces and outputs one X-ray image including image information of bones and soft tissues. The image information of bones and soft tissues included in the X-ray image shows a clear image in which afterimage of image information of bones and soft tissues is removed from each other, allowing the user to observe the conditions of both the bone and the soft tissue from one image and to analyze relation between the bone and the soft tissue.

Hereinafter, an X-ray imaging apparatus according to another exemplary embodiment will be described, based on exemplary embodiments described with reference to FIGS. 1 and 3.

The configuration of the X-ray imaging apparatus according to this exemplary embodiment is the same as that of the exemplary embodiment described with reference to FIGS. 1 and 3, except for the operation of the image generator. In the exemplary embodiment described with reference to FIG. 3, an image generator produces one X-ray image including the image information of the bone and the image information of the soft tissue obtained from the information acquirer. The current exemplary embodiment relates to one X-ray image in which the bones and the soft tissues have different levels of brightness.

In the X-ray imaging apparatus according to this exemplary embodiment, the image generator 313 may include a brightness control filter, which controls a pixel value included in a region corresponding to a bone and in a region corresponding to soft tissue in one X-ray image and thereby makes the brightness of bones different from the brightness of the soft tissue. The region that is brighter among the two regions may be randomly determined by the image generator.

Figure 8A:
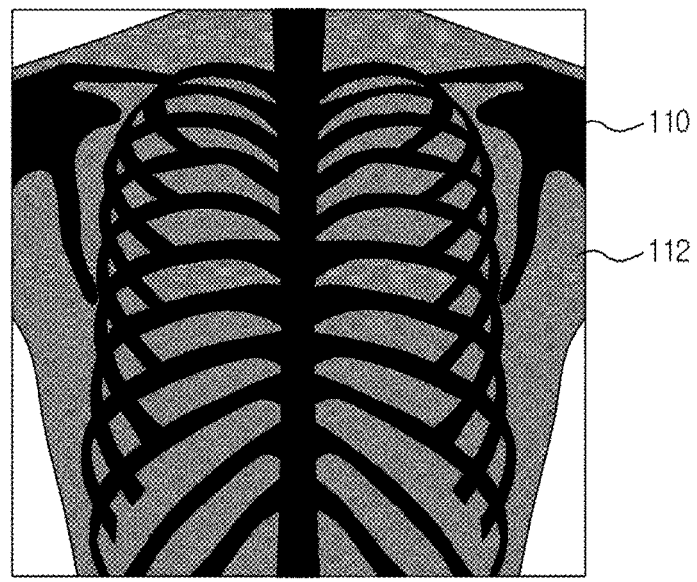
FIGS. 8A and 8B illustrate examples of X-ray images output from an X-ray imaging apparatus according to an exemplary embodiment.
Figure 8B:
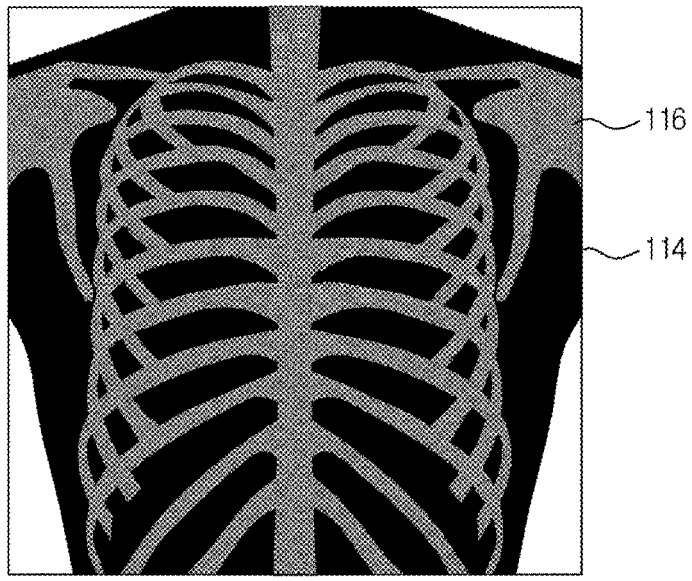

FIGS. 8A and 8B illustrate X-ray images output from an X-ray imaging apparatus according to an exemplary embodiment.

In the X-ray images of FIGS. 8A and 8B, a deep region, that is, a black region is a strongly bright region and a light region, that is, gray region is a weakly bright region.

When the image generator 313 determines to show the bone brighter, the bone region 110 is expressed to be brighter than the soft tissue region 112, as shown in FIG. 8A. The brightness control filter multiplies the values of all of the pixels corresponding to the image information of the bone in one X-ray image including the image information of the bone and the image information of the soft tissue, by a predetermined value, to intensify the visual appearance of the bone.

When the image generator 313 determines to show the soft tissue brighter, the soft tissue region 114 is expressed brighter than the bone region 116, as shown in FIG. 8B. The brightness control filter multiplies the values of all of the pixels corresponding to the image information of the soft tissue in one X-ray image including the image information of the bone and the image information of soft tissue, by a predetermined value, to intensify the visual appearance of the soft tissue.

In this exemplary embodiment, the bone and soft tissue have different levels of brightness. Accordingly, the brightness control filter is capable of controlling any one region of bones and soft tissues to be darker or lighter. That is, in this exemplary embodiment, the bone region and the soft tissue region may be brighter or darker relative to each other.

The exemplary embodiment described above is provided only as an example and any manner or filter may be used so long as it is capable of making bone and soft tissue different from each other in brightness in one image.

Hereinafter, an X-ray imaging apparatus according to another exemplary embodiment will be described.

Figure 9:
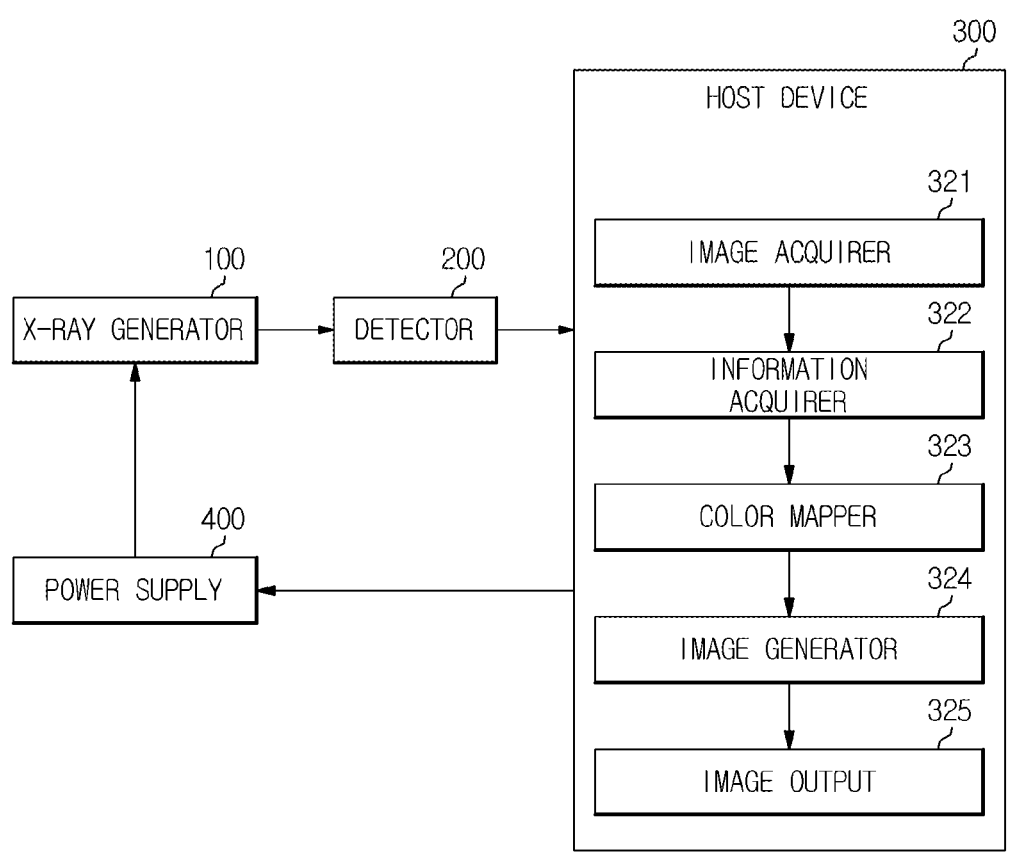
FIG. 9 is a block diagram illustrating an X-ray imaging apparatus according to an exemplary embodiment.

FIG. 9 is a block diagram illustrating an X-ray imaging apparatus according to an exemplary embodiment.

Referring to FIG. 9, the X-ray imaging apparatus according to this exemplary embodiment includes an X-ray generator 100 to generate X-rays having at least two different energy levels to be irradiated to a subject; a power supply 400 to supply power to the X-ray generator 100; a detector 200 to detect the X-rays transmitted through the subject; and a host device 300 to obtain images detected by the detector 200, to obtain respective image information of bones and soft tissues of the subject, based on the obtained X-ray image, to map the obtained image information onto different color channels and thereby produce and output one image including all of the image information.

The X-ray generator 100, power supply 400 and detector 200 of this exemplary embodiment are the same as those of the exemplary embodiment described with reference to FIGS. 1 and 3 and a detailed description thereof is thus omitted.

As shown in FIG. 9, the host device 300 according to this exemplary embodiment includes an image acquirer 321 to perform image-processing of an electrical signal transmitted from the detector 200 to obtain an X-ray image, an information acquirer 322 to obtain image information of bones and soft tissues, based on the obtained X-ray image and attenuation properties of bones and soft tissues, a color mapper 323 to map the image information of bones and soft tissues onto different color channels, an image generator 324 to produce one image including all of image information of bones and soft tissues, and an image output 325 to output the produced image.

The image acquirer 321 and the information acquirer 322 of this exemplary embodiment are same as those of the exemplary embodiment described with reference to FIG. 3 and a detailed description thereof is thus omitted.

The color mapper 323 maps bone image information and soft tissue image information obtained from the information acquirer 322 on different color channels among a plurality of color channels. Generally, an X-ray image is expressed by brightness of black and white using a gray level, instead of the color channel, while this exemplary embodiment maps image information of bones and soft tissues on a color channel to distinguish bones from soft tissues in one image by color. Any color model used for the exemplary embodiment described with reference to FIG. 9 may be used without limitation so long as it renders at least two different colors.

For example, in a case where a red-green-blue (RGB) model is used, the color mapper maps image information of bone and image information of soft tissue onto a red channel and a green channel, respectively. The image generator produces and outputs one image including all of the image information of bone and image information of soft tissue or the red channel and green channel, and the bone and the soft tissue are expressed by a red color and a green color, respectively, in one image, to easily distinguish the bone from the soft tissue.

Alternatively, the image information of bone is mapped onto the red channel and expressed by a red color, while the image information of soft tissue is expressed by a gray level.

Figure 10:
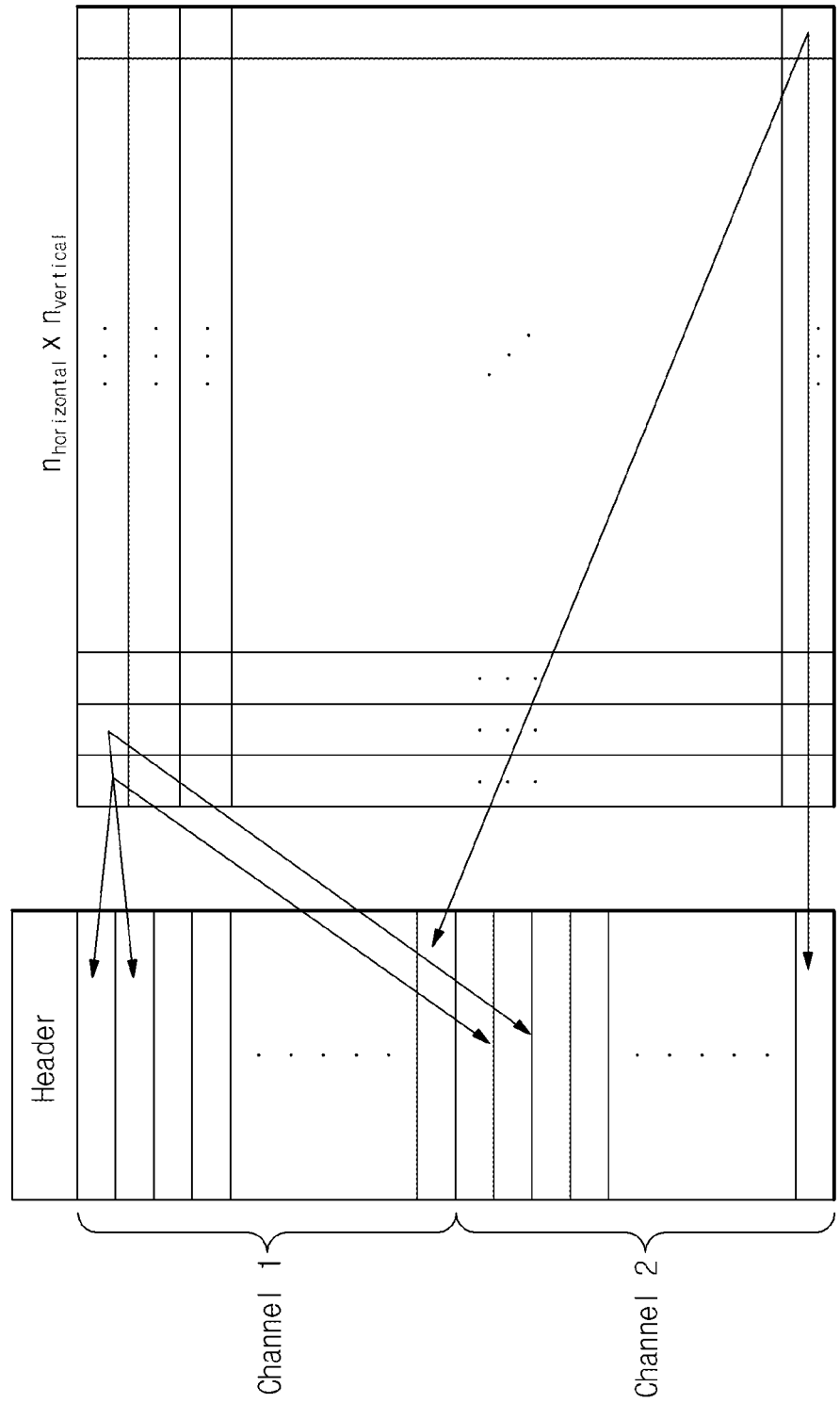
FIG. 10 is a schematic view illustrating a data structure of one image produced from the X-ray imaging apparatus according to an exemplary embodiment.

FIG. 10 is a schematic view illustrating a data structure of one image produced according to the exemplary embodiment described with reference to FIG. 9.

Referring to FIG. 10, one image produced by the image generator 324 may be divided into a plurality of pixels and each pixel includes image information of bones and soft tissues. Accordingly, when the image information of bones and image information of soft tissues are mapped onto the color channels having different colors, such as channel 1 and channel 2, respectively, as shown in FIG. 10, the image information of each pixel is stored in the corresponding color channel.

The data structure shown in FIG. 10 is provided only as an example and a manner in which the image information of bones and soft tissues are mapped onto the color channel or a color mapped-data structure are not limited to the aforementioned examples.

Figure 11:
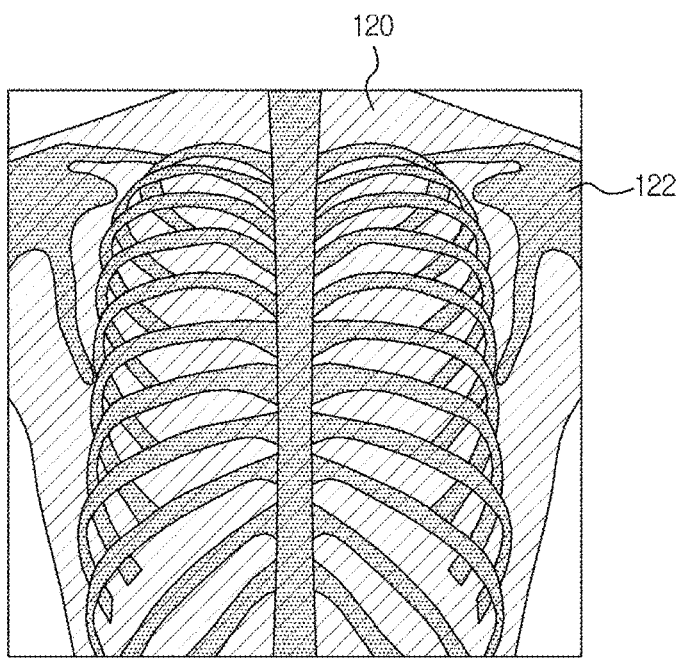
FIG. 11 is a schematic view illustrating an example of an X-ray image produced and output from the X-ray imaging apparatus according to an exemplary embodiment.

FIG. 11 is a schematic view illustrating an X-ray image produced and output according to the exemplary embodiment described with reference to FIG. 9.

In the X-ray image of FIG. 11, a diagonal-line pattern 120 is expressed by a green color and a dot pattern 122 is expressed by a red color. Thus, the soft tissues are expressed by a green color, while the bones, such as a rib, scapula and spine, are expressed by a red color. In addition, a region where bones overlap soft tissues exhibits a mixed color of red and green, and when the density of bones is high, the red color is strong, and when the density of soft tissues is high, the green color is strong. The user can appreciate a level of bones and soft tissues present in the region through the color of the corresponding region. It is noted that the diagonal-line pattern and dot pattern of FIG. 11 exhibit a difference in color without concentration or density in the X-ray image.

For example, the user observes an X-ray image showing both bones and soft tissues through the image output 325 and then more accurately analyzes only one of the X-ray image of bones and the X-ray image of soft tissues. Hereinafter, an X-ray imaging apparatus to selectively produce and output an X-ray image of bone or soft tissue according to an exemplary embodiment will be described.

Figure 12:
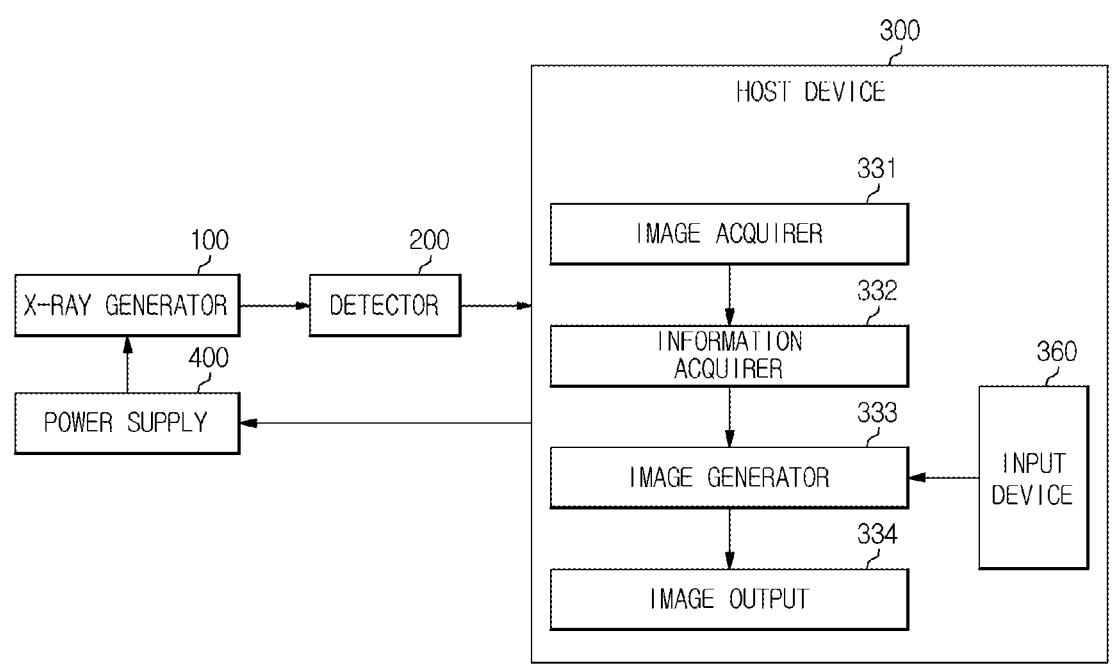
FIG. 12 is a block diagram illustrating an X-ray imaging apparatus according to an exemplary embodiment.

FIG. 12 is a schematic block diagram illustrating an X-ray imaging apparatus according to an exemplary embodiment.

Referring to FIG. 12, the X-ray imaging apparatus according to this exemplary embodiment includes an X-ray generator 100 to generate X-rays having at least two different energy levels to be irradiated to a subject; a power supply 400 to supply power to the X-ray generator 100; a detector 200 to detect the X-rays transmitted through the subject; and a host device 300 to produce and output one image including image information of bones and soft tissues and to produce and output an X-ray image including only one of the image information of the bone and the image information of the soft tissue, according to a selection of the user.

The operations of the X-ray generator 100, power supply 400 and detector 200 of this exemplary embodiment are the same as those of the exemplary embodiment described with reference to FIGS. 1 and 3 and a detailed description thereof is thus omitted.

The host device 300 includes an image acquirer 331 to perform image-processing of an electrical signal transmitted from the detector 200 to obtain an X-ray image, an information acquirer 332 to obtain image information of bone and soft tissue, based on the obtained X-ray image and attenuation properties of bone and soft tissue, an input device 360 to receive a selection of a user, an image generator 333 to produce one image including image information of bone and soft tissue, and an image output 334 to produce one image including only image information of one of bone and soft tissue.

The operations of the image acquirer 331 and information acquirer 332 of this exemplary embodiment are the same as those of the exemplary embodiment described with reference to FIG. 3 and a detailed description thereof is thus omitted.

The image generator 333 first produces a combined X-ray image including image information of bone and soft tissue, similar to the exemplary embodiment described with reference to FIG. 3, and the image output 334 outputs this X-ray image.

The user can confirm conditions of bone and soft tissue from the output image and, as a result, more accurately analyzes a region in which abnormal bone or soft tissue is present. The input device 360 is used to input a selection of a bone or soft tissue and may be a mouse, keyboard, touch panel or the like, of the host device 300.

When the user inputs selection using the input device 360, the image generator 333 produces an X-ray image including only image information of a selected bone or soft tissue and the image output 334 outputs the produced X-ray image. For example, when the user selects the bone, the image generator 333 produces an X-ray image including only the image information of the bone and outputs the X-ray image through the image output 334, and when the user selects soft tissue, the image generator 333 produces an X-ray image including only image information of the soft tissue and outputs the X-ray image through the image output 334.

In this exemplary embodiment, after the X-ray image including image information of the bone and soft tissue is produced and output as described above with reference to FIGS. 1 and 3, the input device 360 may receive a selection of the user, and the image generator may further output an X-ray image including only image information of the selected bone or soft tissue.

As described above with reference to FIG. 8, the X-ray imaging apparatus designates one among bone and soft tissue through the image generator and makes a region corresponding to bones or soft tissues designated in one image to be brighter or lighter.

An X-ray imaging apparatus may include an input device, in addition to components of the X-ray imaging apparatus according to an exemplary embodiment described with reference to FIG. 8, and the image generator may make a region corresponding to bones or soft tissues selected by the user to be brighter according to the user's selection.

Also, in addition to components of the X-ray imaging apparatus according to the exemplary embodiment described with reference to FIG. 9, an exemplary embodiment that is described below with reference to FIG. 13, further includes an input device to input selection of bone or soft tissue by a user and further output the X-ray image. Hereinafter, this exemplary embodiment will be described in detail.

Figure 13:
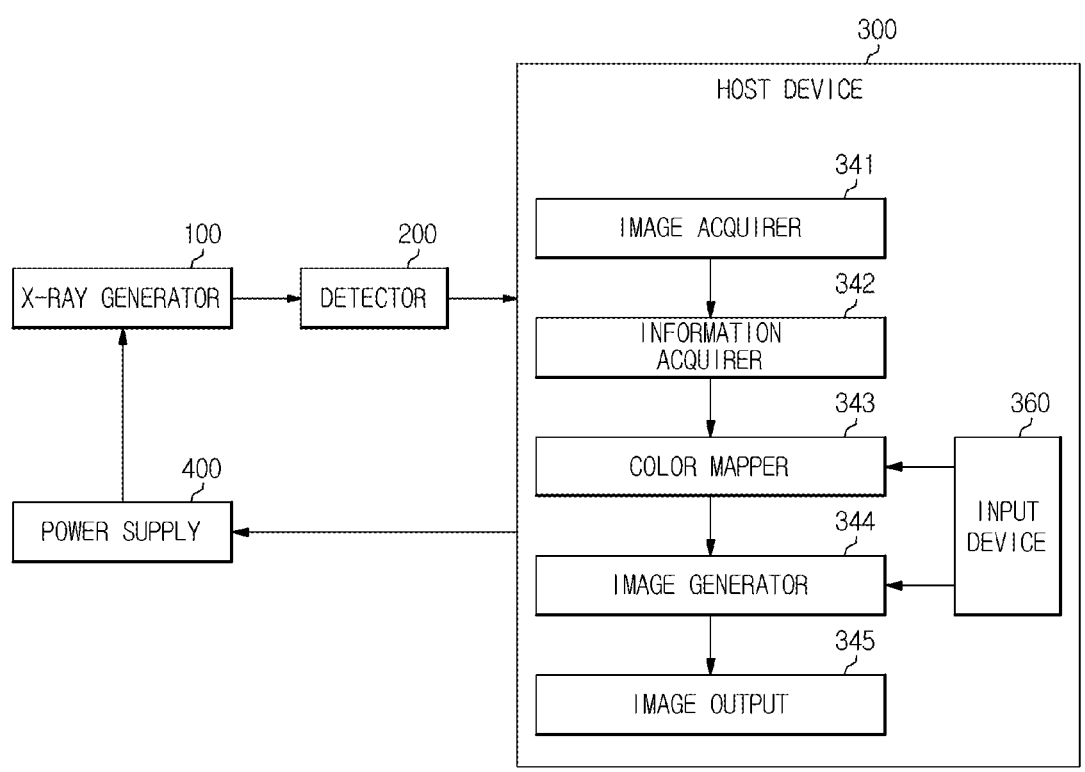
FIG. 13 is a block diagram illustrating an X-ray imaging apparatus according to an embodiment.

FIG. 13 is a block diagram illustrating an X-ray imaging apparatus according to an exemplary embodiment.

Referring to FIG. 13, the X-ray imaging apparatus according to this exemplary embodiment includes an X-ray generator 100 to generate X-rays having at least two different energy levels to be irradiated to a subject; a power supply 400 to supply power to the X-ray generator 100; a detector 200 to detect the X-rays transmitted through the subject; and a host device 300 to obtain images detected by the detector 200, to obtain respective image information of bone and soft tissue of the subject, based on the obtained X-ray image, to map the obtained plurality of image information onto different color channels, to produce and output one image including all image information, and to thereby produce and output one image including only image information of bone or soft tissue selected by the user.

The operations of the X-ray generator 100, power supply 400 and detector 200 of this exemplary embodiment are the same as those of the exemplary embodiments described with reference to FIGS. 1 and 3 and a detailed description thereof is thus omitted.

The host device 300 of this exemplary embodiment includes an image acquirer to obtain an X-ray image through image-processing of an electrical signal transferred from the detector 200, an information acquirer to obtain image information of bone and soft tissue, based on the obtained X-ray image and difference in attenuation between bone and soft tissue, an image generator to produce an image including all of the obtained image information, an image output to output the produced image, and an input device to receive a selection of an user.

The image acquirer 341, information acquirer 342 and color mapper 343 of this exemplary embodiment operate in the same manner as in the exemplary embodiment described with reference to FIG. 9. The image generator 344 and the image output 345 produce and output one X-ray image including all of image information of bone and soft tissue in the same manner as in the exemplary embodiment described with reference to FIG. 9, and further operate depending on a user selection through the input device 360.

The input device 360 receives a user's selection for an X-ray image including only the image information of the bone or an X-ray image including only image information of the soft tissue, and directly inputs selection of the bone or the soft tissue or indirectly inputs selection via selection of the color channels mapped with the image information of the bone and soft tissue.

Also, the input device 360 inputs selection of color mapping by a user, for example, the user selects mapping of bone onto a red channel and mapping of soft tissue onto a green channel, or mapping of bone onto the green channel and mapping of soft tissue onto the blue channel. The color mapper maps image information and color channel depending on user selection.

For example, when the image information of bone is mapped onto the red channel and image information of soft tissue is mapped onto the green channel, the user can select the red or green channel through the input device.

The image generator produces one X-ray image including only image information of bone or soft tissue selected by the user and outputs the image through the image output 345. For example, when the user selects soft tissue, the image generator produces one X-ray image including only image information of the soft tissue, and when the user selects a green channel mapped onto soft tissue, the image generator 344 produces one X-ray image only including the green channel.

The X-ray image including only a green channel is the same as an X-ray image including only image information of soft tissue, and direct selection of bone or soft tissue and indirect selection via the color channel are only different from each other in terms of input manner of input device and produce substantially identical results.

Figure 14A:
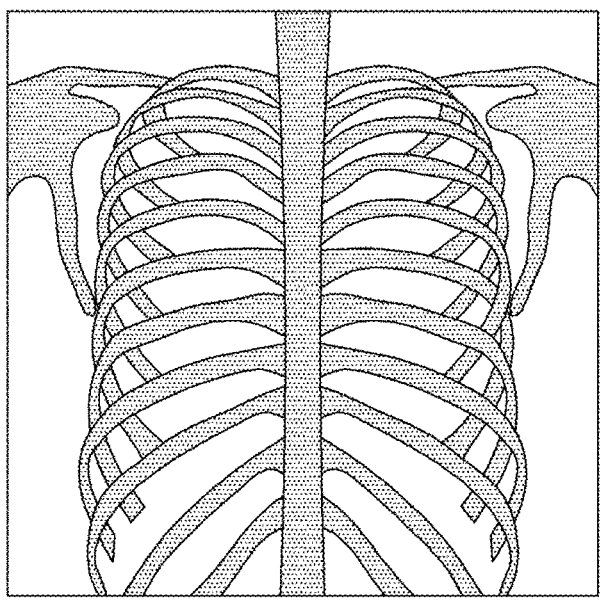
FIGS. 14A and 14B illustrate an example of an X-ray image output by the X-ray imaging apparatus according to an exemplary embodiment.
Figure 14B:
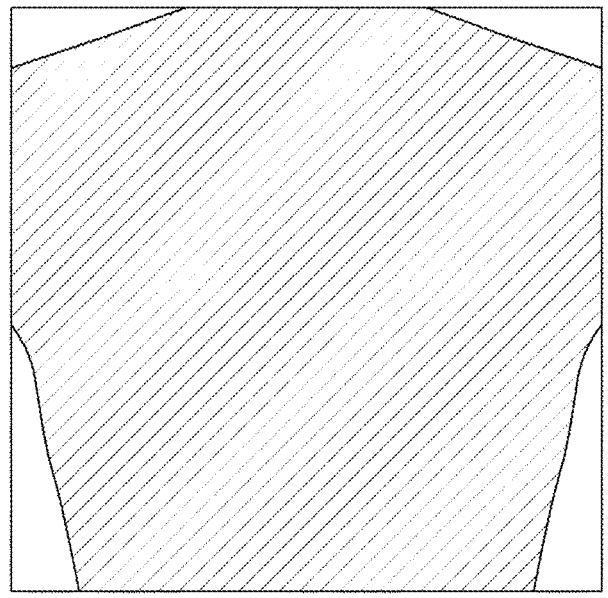

FIGS. 14A and 14B illustrate X-ray images output by the X-ray imaging apparatus according to the exemplary embodiment described with reference to FIG. 13.

The X-ray imaging apparatus according to this exemplary embodiment first outputs an X-ray image of FIG. 11 discussed above, receives a selection of a user through the input device, and outputs an X-ray image according to the selection. When the user selects bone or a red channel mapped with image information of bone, an X-ray image including only image information of the bone is produced and output, as shown in FIG. 14A, and only the bone expressed by a red color is observed in the X-ray image. On the other hand, when the user selects the soft tissue or a green channel mapped with image information of soft tissue, as shown in FIG. 14B, an X-ray image including only image information of the soft tissue is produced and output and only the soft tissue expressed by a green color is observed in the X-ray image.

The user can obtain information associated with a test site of the subject in need of more detailed analysis from the X-ray image shown in FIGS. 14A and 14B.

This exemplary embodiment is similar to the exemplary embodiment associated with the X-ray imaging apparatus described with reference to FIG. 8 and can make the selected region relatively brighter. Referring to the block diagram of FIG. 13, when the user selects any one of bone and soft tissue through the input device 360, this exemplary embodiment makes a region corresponding to a selected bone or soft tissue brighter than a non-selected region in the one image produced by the image generator 344. The image generator may include a brightness control filter.

The image output 345 may output an image with a controlled brightness and the user may more accurately observe the desired test site through the output image and, at the same time, can confirm a relation between the selected region and the non-selected region.

The X-ray imaging apparatuses according to exemplary embodiments described above produce and output one X-ray image including all of image information of bone and soft tissue, and further produce and output one X-ray image including only image information of bone or soft tissue. In the X-ray imaging apparatus according to an exemplary embodiment that will be described with reference to FIG. 15, the user can change a weight of the bone and soft tissue in the same X-ray image.

The X-ray imaging apparatus according to this exemplary embodiment includes an X-ray generator 100, a power supply 400, a detector 200 and a host device 300, and the operations of the X-ray generator 100, the power supply 400 and the detector 200 are the same as those of the exemplary embodiment described with reference to FIG. 12 and a detailed description thereof is thus omitted.

The host device 300 includes an image acquirer 331, an information acquirer 332, an image generator 333, an input device 360 and an image output 334. Operations of the image acquirer and information acquirer of this exemplary embodiment are also the same as those of the exemplary embodiment described with reference to FIG. 12.

The image generator 333 produces and outputs one image including all of image information of bone and soft tissue, and the input device 360 receives user instructions associated with variation in weight of bone and soft tissue. The input device may be a keyboard, mouse or touch panel or a predetermined member movable or rotatable by the user.

Figure 15:
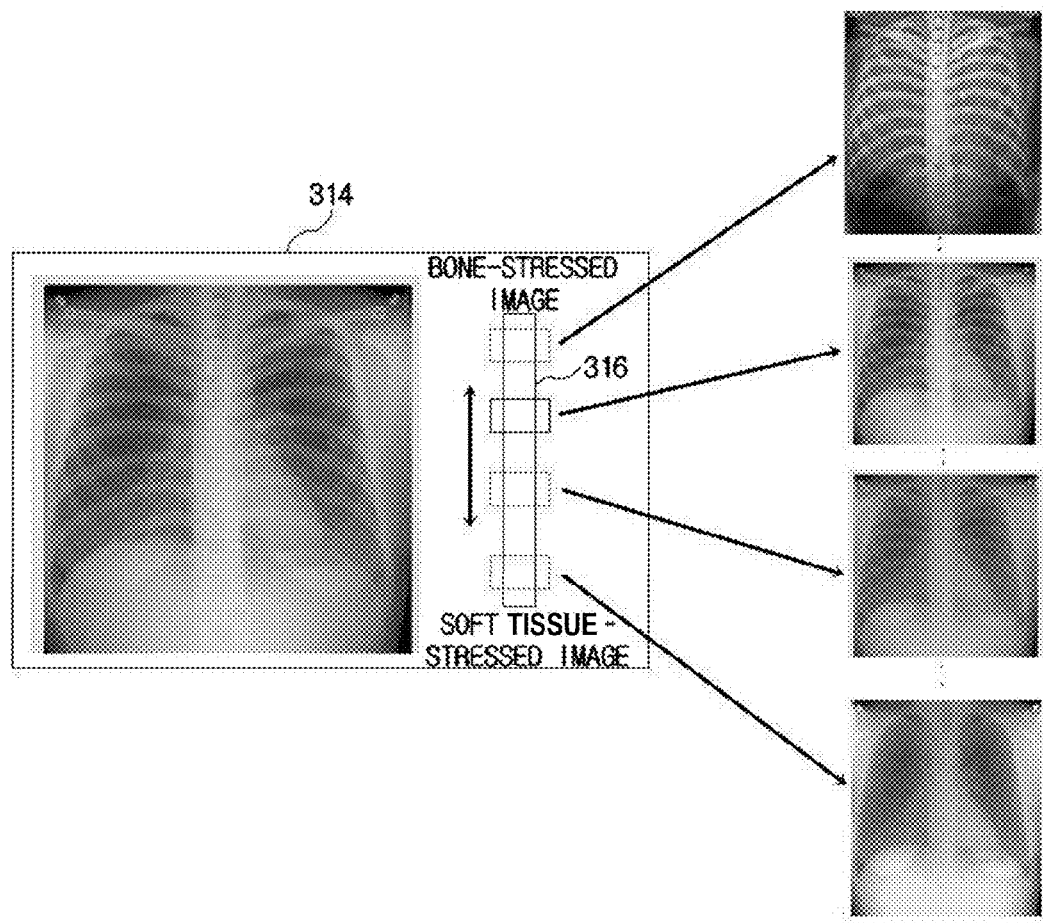
FIG. 15 illustrates an image output on a screen of an X-ray imaging apparatus according to an exemplary embodiment.

FIG. 15 illustrates an image output by an X-ray imaging apparatus according to an exemplary embodiment.

Referring to FIG. 15, the image generator produces one X-ray image including image information of bone and soft tissue, based on a weight ratio of bone and soft tissue of 1:1 and outputs the image on a screen 314 of the image output. The output of image through the image output is performed after generation of the image by the image generator and the detailed description of this process will be omitted.

The image output outputs an X-ray image having a weight ratio of 1:1 together with a control bar 316 as shown in FIG. 15. The control bar can move up and down and the user can move the control bar using a cursor of a mouse or a keyboard arrow or through touch by hand when the image output is a touch panel.

When the first output image is an image having a weight ratio of 1:1, as the control bar is moved up, the weight of the bone increases, and when the control bar is moved down, the weight of the soft tissue increases and vice versa. In FIG. 15, an X-ray image displayed on the left of the screen 314 is changed to an X-ray image displayed on the right thereof according to movement of control bar, and variation in weight is continuous and variation in X-ray image is thus also continuous.

As shown on the right side of FIG. 15, as the control bar moves up, the bones are stressed in the X-ray image, and, as the control bar moves down, the soft tissues are stressed. The user observes and confirms an output X-ray image and selects the desired X-ray image, while moving a control bar.

FIG. 15 is provided only as an exemplary embodiment, and a weight ratio of an initially output image may be different from 1:1. Also, the configuration of the image output is not limited to the configuration shown in FIG. 15.

For example, the described-above varied weight ratio may be applied to an exemplary embodiment described with reference to FIG. 9. For example, the image generator produces one image including all of mapped color channels, outputs the image through the image generator and, when the user inputs instructions associated with variation in weight of the bone and soft tissue through the input device, a weight ratio of bone to soft tissue is controlled in the X-ray image displayed by the image output. The X-ray image output by the image output may be similar to the X-ray image of FIG. 15, except that a color is mapped on the bone and soft tissue.

Hereinafter, a method for controlling an X-ray imaging apparatus according an exemplary embodiment will be described.

Figure 16:
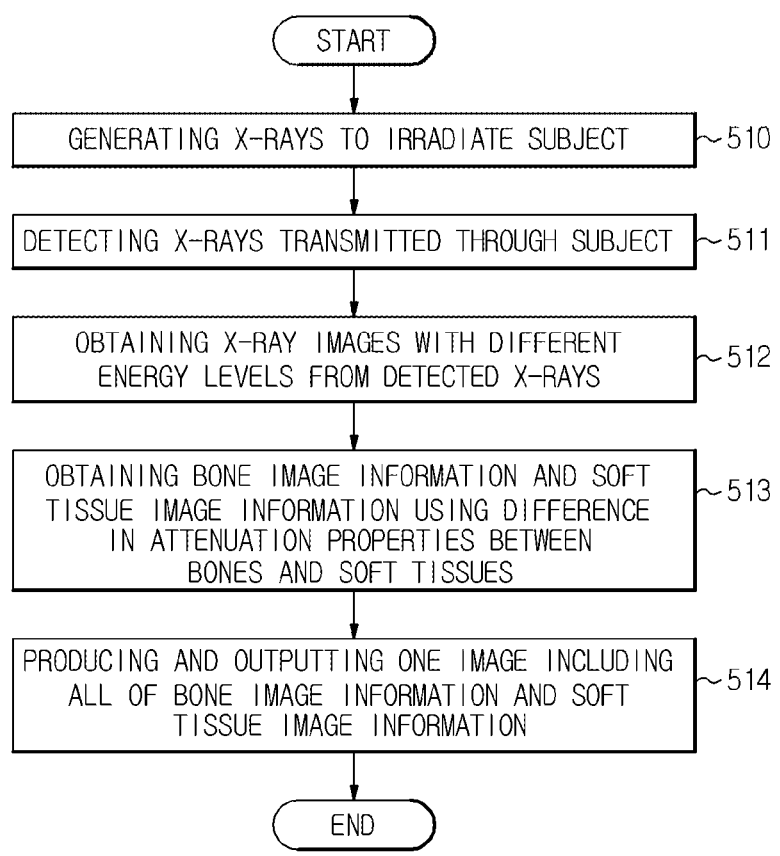
FIG. 16 is a flowchart illustrating a method for controlling an X-ray imaging apparatus according to an exemplary embodiment.

FIG. 16 is a flowchart illustrating a method for controlling an X-ray imaging apparatus according to an exemplary embodiment.

Referring to FIG. 16, an X-ray is generated and irradiated to a subject, in operation 510. The X-ray transmitted through the subject is detected, in operation 511. X-ray images having respective energies are obtained based on the detected X-ray, in operation 512. The energy means an energy having different levels.

Image information of bone and soft tissue are obtained from the obtained X-ray image, using difference in attenuation properties of bone and soft tissue, in operation 513, and one image including all of image information of bone and soft tissue is produced and output, in operation 514.

Similar to the X-ray imaging apparatus as described above, in order to obtain X-ray images having different energy levels, the X-rays having different energy levels are separately irradiated, or an X-ray having a predetermined energy level is irradiated once, and the X-ray is then separated from X-rays having different energy levels using PCD. In an exemplary embodiment, the two methods may be used.

Hereinafter, an exemplary embodiment using separate irradiation of X-rays having different energy levels will be described.

Figure 17:
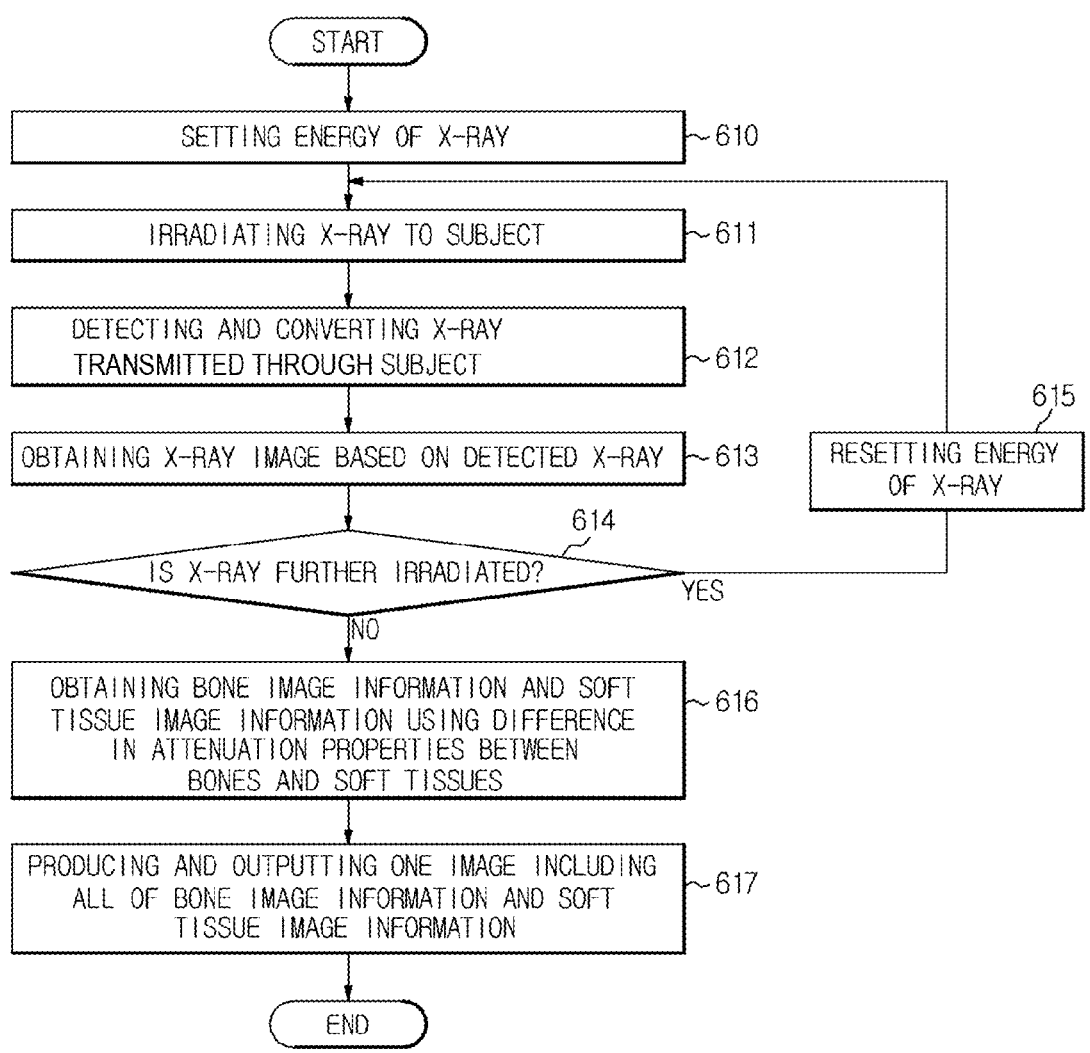
FIG. 17 is a flowchart illustrating a method for controlling the X-ray imaging apparatus according to an exemplary embodiment.

FIG. 17 is a flowchart illustrating a method for controlling an X-ray imaging apparatus according to an exemplary embodiment.

Referring to FIG. 17, an energy of X-ray to be irradiated is set, in operation 610. An X-ray having a predetermined energy is irradiated onto a subject by supplying power corresponding to the set energy to the X-ray generator 100, in operation 611. The value of set energy depends on the area for which a diagnosis is sought. For example, in breast imaging, an X-ray having a high energy is primarily irradiated by supplying a tube voltage of 110 kVp and a tube current of 120 mA.

The detector 200 detects the X-ray transmitted through the subject and converts the X-ray into an electrical signal, in operation 612. The image acquirer obtains an X-ray image, based on the detected X-ray, in operation 613. That is, the converted electrical signal is transmitted to the host device 300 and the image acquirer obtains an X-ray image through image-processing of the electrical signal.

In operation 614, it is determined whether an X-ray is to be further irradiated. An exemplary embodiment relates to an X-ray imaging apparatus which performs irradiation of X-ray at least two times and the number of irradiations depends on the number of energy levels to be used.

As a result of the determination, when an X-ray is to be further irradiated ("yes"), the energy level of X-ray to be irradiated is reset such that it is different from the energy level of the previously irradiated X-ray, in operation 615, and an X-ray having the reset energy level is irradiated to a subject, in operation 611. Also, the detection of X-ray using the detector 200 and obtaining an X-ray image using the image acquirer are repeated.

Unless an X-ray is further irradiated, the information acquirer obtains image information of bone and soft tissue from the obtained X-ray image using difference in X-ray attenuation properties of bone and soft tissue, in operation 616.

The image generator produces one X-ray image including all of the obtained bone image information and soft tissue image information and outputs the X-ray image through the image output, in operation 617.

Figure 18:
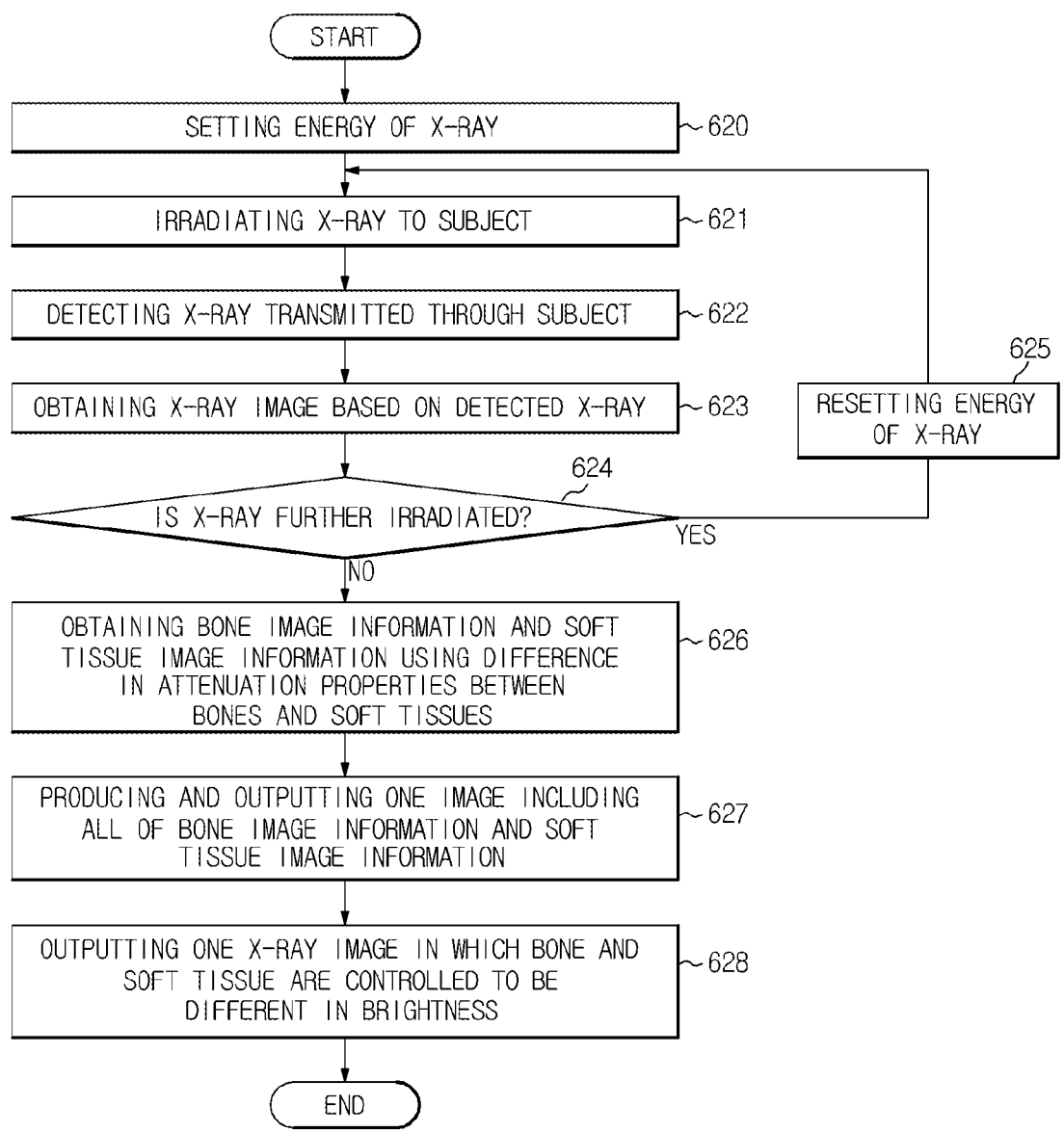
FIG. 18 is a flowchart illustrating a method for controlling the X-ray imaging apparatus according to an exemplary embodiment.

FIG. 18 is a flowchart illustrating a method for controlling the X-ray imaging apparatus according to the exemplary embodiment described with reference to FIG. 8.

Similarly to an exemplary embodiment described above with reference to FIG. 17, an energy of X-ray is set, in operation 620, the X-ray is irradiated to the subject, in operation 621, the X-ray transmitted through the subject is detected and converted into an electrical signal, in operation 622, an X-ray image is obtained through image-processing, in operation 623, and whether further to irradiate an X-ray is determined, in operation 624. When an X-ray is further irradiated, the energy level of X-ray to be irradiated is reset such that it is different from the energy level of the previously irradiated X-ray, in operation 625, and the aforementioned process is repeated with the reset energy of X-ray.

The information acquirer obtains image information of bone and soft tissue from the obtained X-ray image using difference in X-ray attenuation properties between bone and soft tissue, in operation 626, and the image generator produces one image including all of image information of bone and soft tissue, in operation 627.

A bone region and a soft tissue region are controlled to be different from each other in brightness in one image. Specifically, the image generator makes one of the bone and soft tissue region brighter or darker than the other region using a brightness control filter. This aims to distinguish bone from soft tissue in one X-ray image using difference in brightness levels. The bone region and soft tissue region may be different from each other and any of the bone region or the soft tissue region may be brighter or darker.

The X-ray image in which bone and soft tissue are controlled to be different in brightness is output through the image output, in operation 628.

Figure 19:
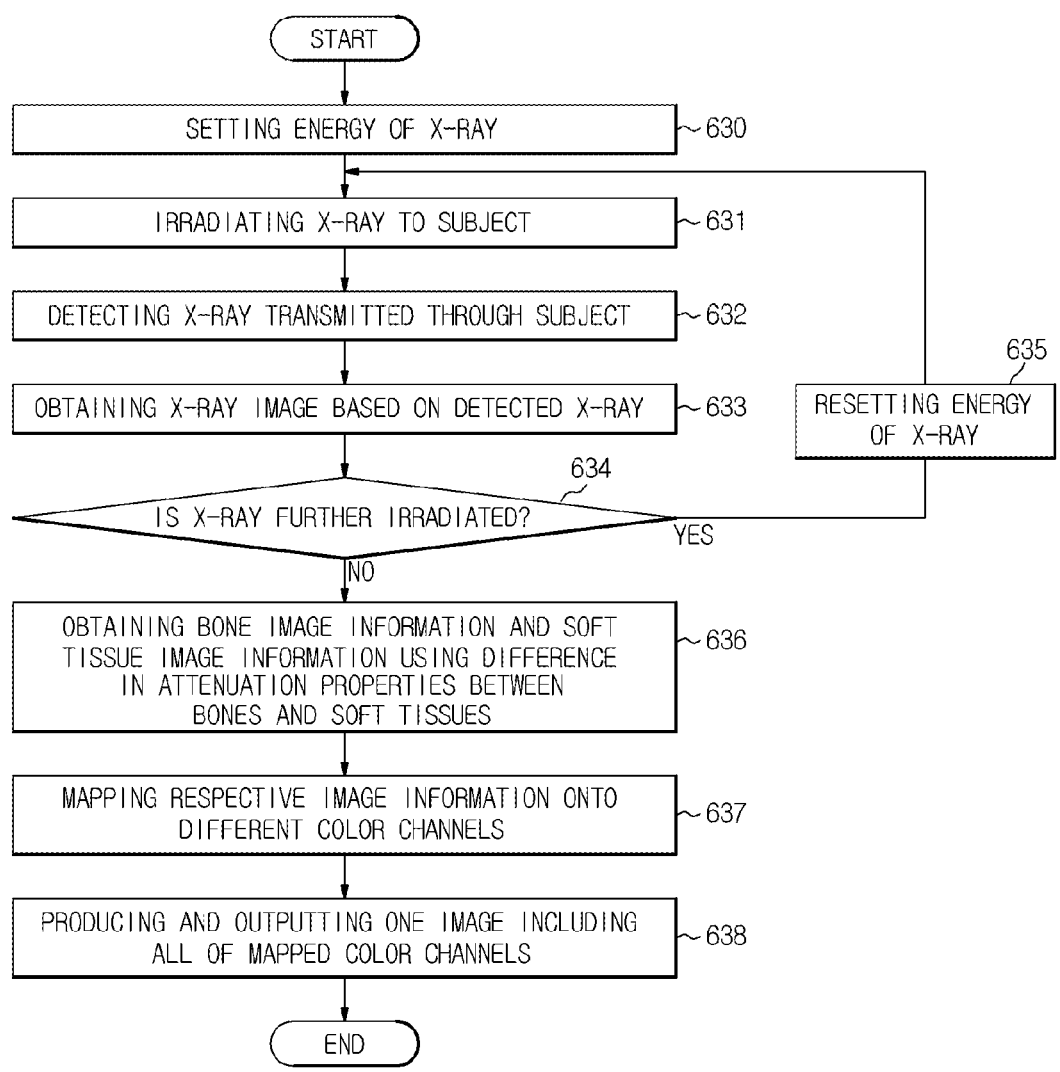
FIG. 19 is a flowchart illustrating a method for controlling the X-ray imaging apparatus according to an exemplary embodiment.

FIG. 19 is a flowchart illustrating a method for controlling the X-ray imaging apparatus according to the exemplary embodiment described with reference to FIG. 9.

Similarly to what is described above, an energy of X-ray is set, in operation 630, the X-ray is irradiated to a subject, in operation 631, the X-ray transmitted through the subject is detected and converted into an electrical signal, in operation 632, an X-ray image is obtained through image-processing, in operation 633, whether further to irradiate an X-ray is determined, in operation 634, and the aforementioned process is repeated while resetting an energy level of X-ray, in operation 635.

The information acquirer obtains image information of bone and soft tissue from the obtained X-ray image using difference in X-ray attenuation properties between bone and soft tissue, in operation 636, and the color mapper maps obtained respective image information onto different color channels, in operation 637. A detailed explanation of color mapping is described above with reference to FIG. 9.

The image generator produces one image including all of mapped color channels and outputs the image through the image output, in operation 638. That is, the image generator produces and outputs one image including all of image information of the bone and soft tissue. A user can simultaneously determine conditions of the bone and soft tissue through one X-ray image in which the bone and soft tissue are represented by different colors.

Figure 20:
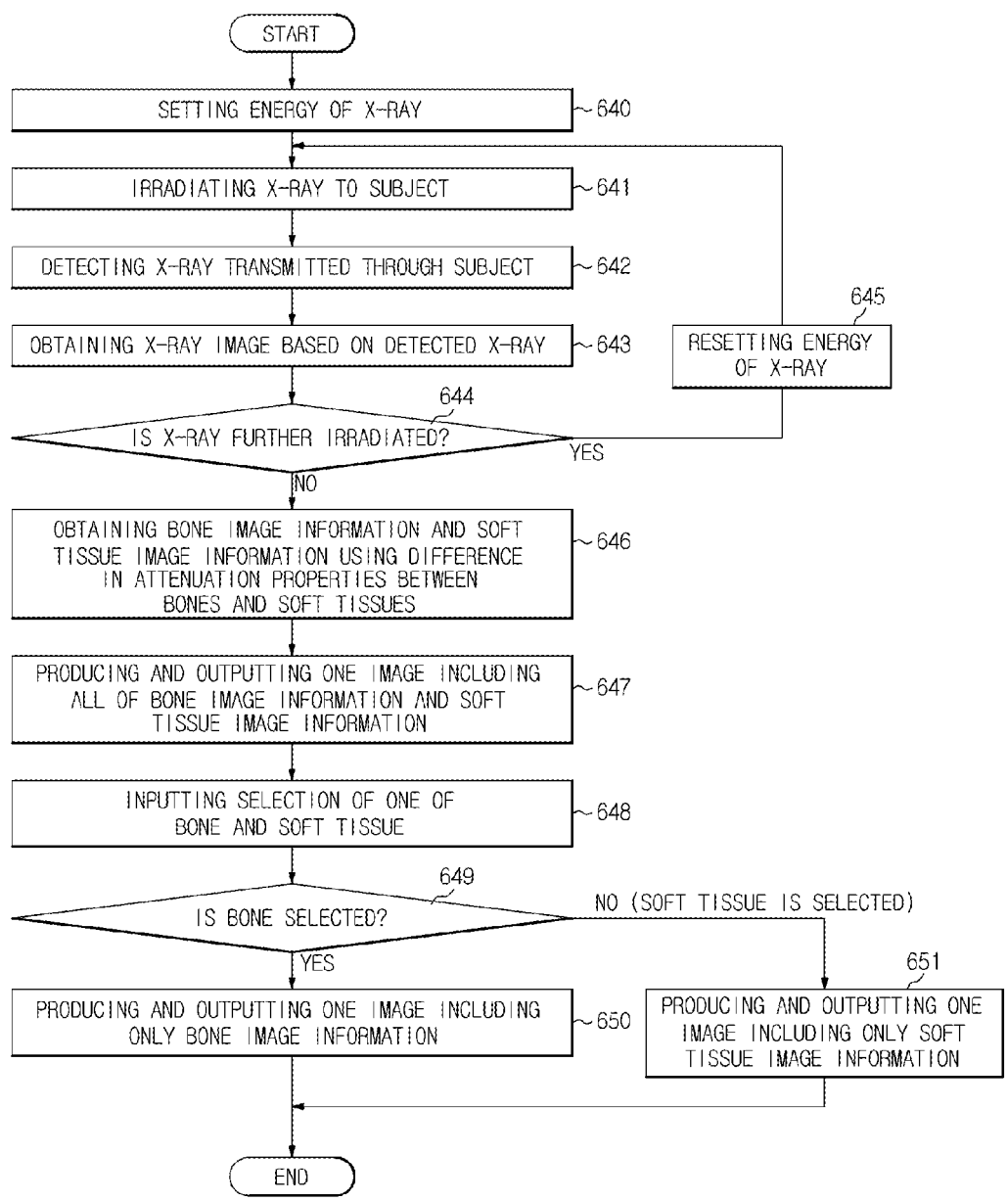
FIG. 20 is a flowchart illustrating a method for controlling the X-ray imaging apparatus according to an exemplary embodiment.

FIG. 20 is a flowchart illustrating a method for controlling the X-ray imaging apparatus according to the exemplary embodiment described with reference to FIG. 12.

The operations 640, 641, 642, 643, 644, 645, 646, and 647 correspond to the respective operations 620 to 627 of an exemplary embodiment described with reference to FIG. 18 and a detailed description thereof is thus omitted.

After one image including all of image information of the bone and soft tissue is output, a user selects one from bone and soft tissue, in operation 648. In operation 649, it is determined whether the user selected the bone ("yes"), and an X-ray image including only image information of the bone is produced and output, in operation 650. If it is determined that the user selected soft tissue, in operation 649 ("No"), one X-ray image including only image information of the soft tissue is produced and output, in operation 651.

Figure 21:
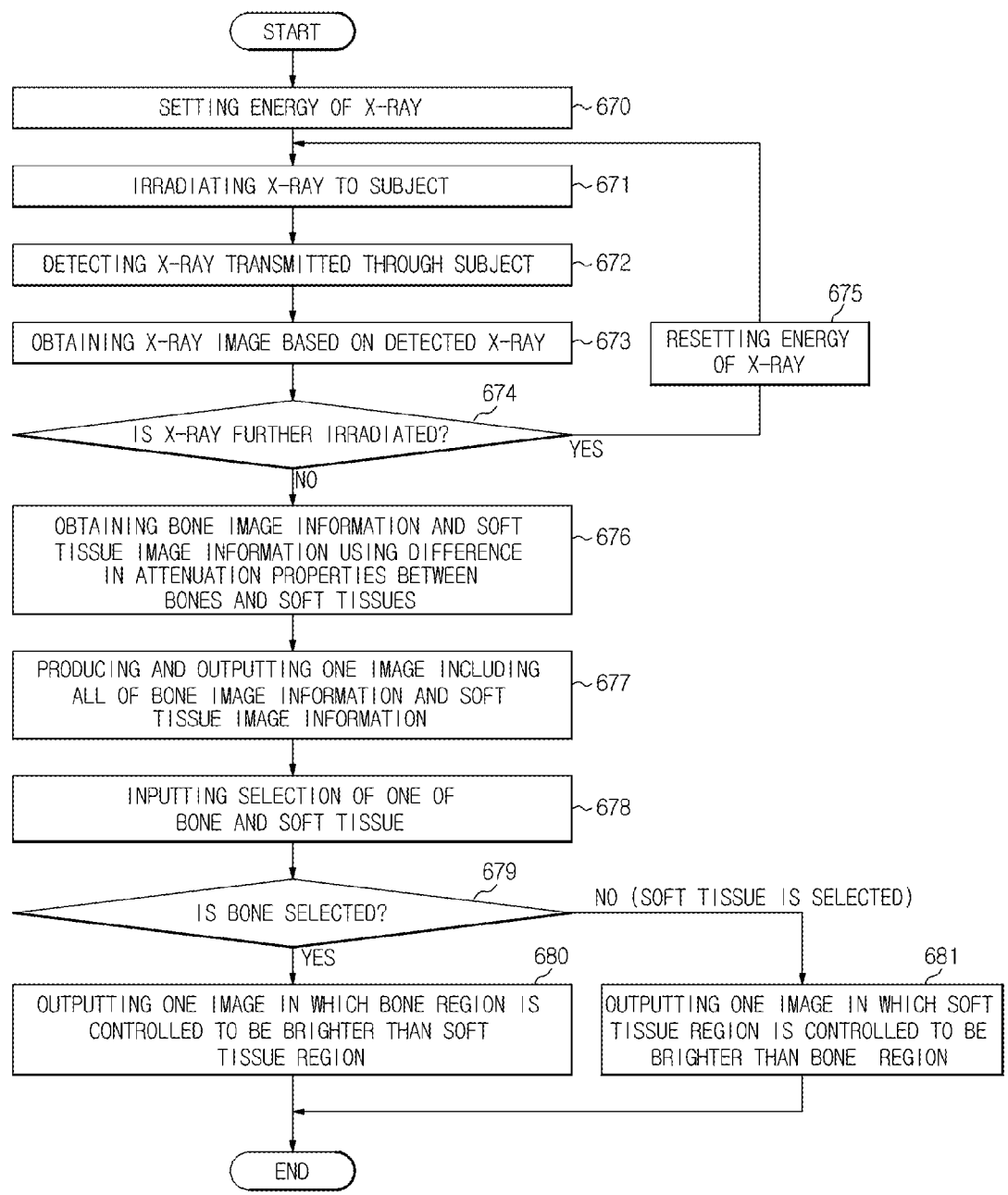
FIG. 21 is a flowchart illustrating a method for controlling the X-ray imaging apparatus according to an exemplary embodiment.

FIG. 21 is a flowchart illustrating a method for controlling the X-ray imaging apparatus according to an exemplary embodiment.

Similar to what is described above, an energy of X-ray is set, in operation 670, the X-ray is irradiated to the subject, in operation 671, the X-ray transmitted through the subject is detected and converted into an electrical signal, in operation 672, an X-ray image is obtained through image-processing, in operation 673, whether further to irradiate an X-ray is determined, in operation 674, and the aforementioned process is repeated while resetting an X-ray energy level, in operation 675.

The information acquirer obtains image information of bone and soft tissue from the obtained X-ray image using difference in X-ray attenuation properties between the bone and soft tissue, in operation 676, and the image generator produces and outputs one image including all of image information of the bone and soft tissue, in operation 677.

The user inputs selection of one from bone and soft tissue, in operation 678. In operation 679, it is determined whether the user selected the bone ("yes"). Accordingly, in one image, a region corresponding to the bone is controlled to be output brighter than a region corresponding to soft tissue, in operation 680. If it is determined that the user selected the soft tissue, in operation 679, the region corresponding to the soft tissue is controlled to be output brighter than the region corresponding to the bone, in operation 681. The brightness of the bone and soft tissue may be relative to each other and brightness of the region corresponding to a non-selected bone or soft tissue may be reduced in order to brighten the region corresponding to a selected bone or soft tissue.

Figure 22:
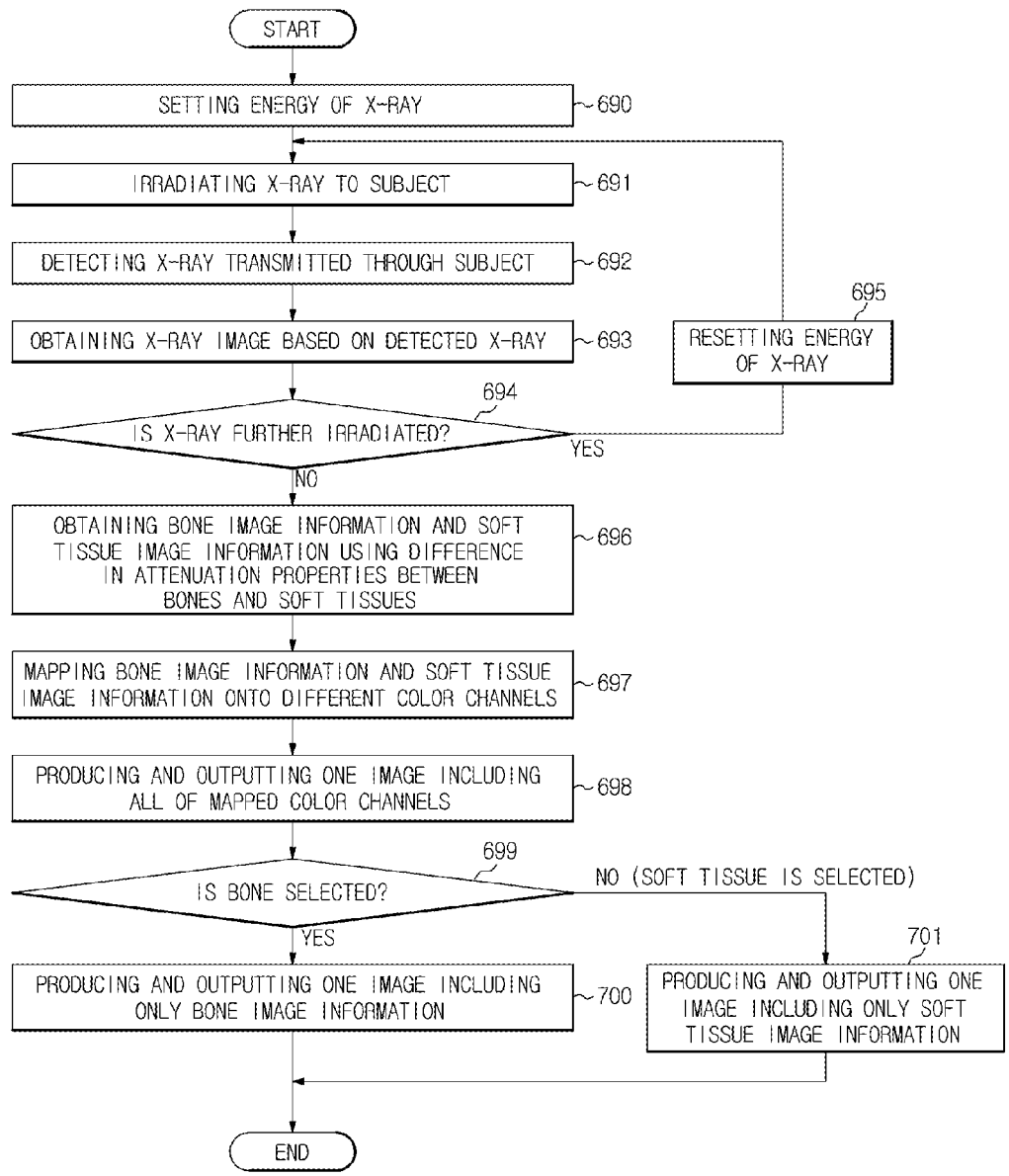
FIG. 22 is a flowchart illustrating a method for controlling an X-ray imaging apparatus according to an exemplary embodiment.

FIG. 22 is a flowchart illustrating a method for controlling an X-ray imaging apparatus according to the exemplary embodiment described with reference to FIG. 13.

The operations 690, 691, 692, 693, 694, 695, 696, 697, and 698 correspond to the operations 630 to 638, respectively, described above with reference to FIG. 19 and a detailed description thereof is thus omitted.

Accordingly, the X-ray image in which the bone and soft tissue are distinguished from each other via different colors is produced and output, in operation 698. In operation 699, in a user may select one from the bone and soft tissue. When the user inputs a selection of the bone ("yes"), an X-ray image including only the image information of the bone is produced and output, in operation 700. When the user inputs selection of soft tissue, in operation 699 ("No"), an X-ray image including only image information of the soft tissue is produced and output, in operation 701.

When the user inputs a selection, the user may select, rather than one of bone and soft tissue, one of the color channels mapped with the bone and soft tissue, respectively. In this case, one X-ray image including only the selected color channel is produced and output, and the results thus obtained are the same as those of the case in which bone or soft tissue are selected.

Figure 23:
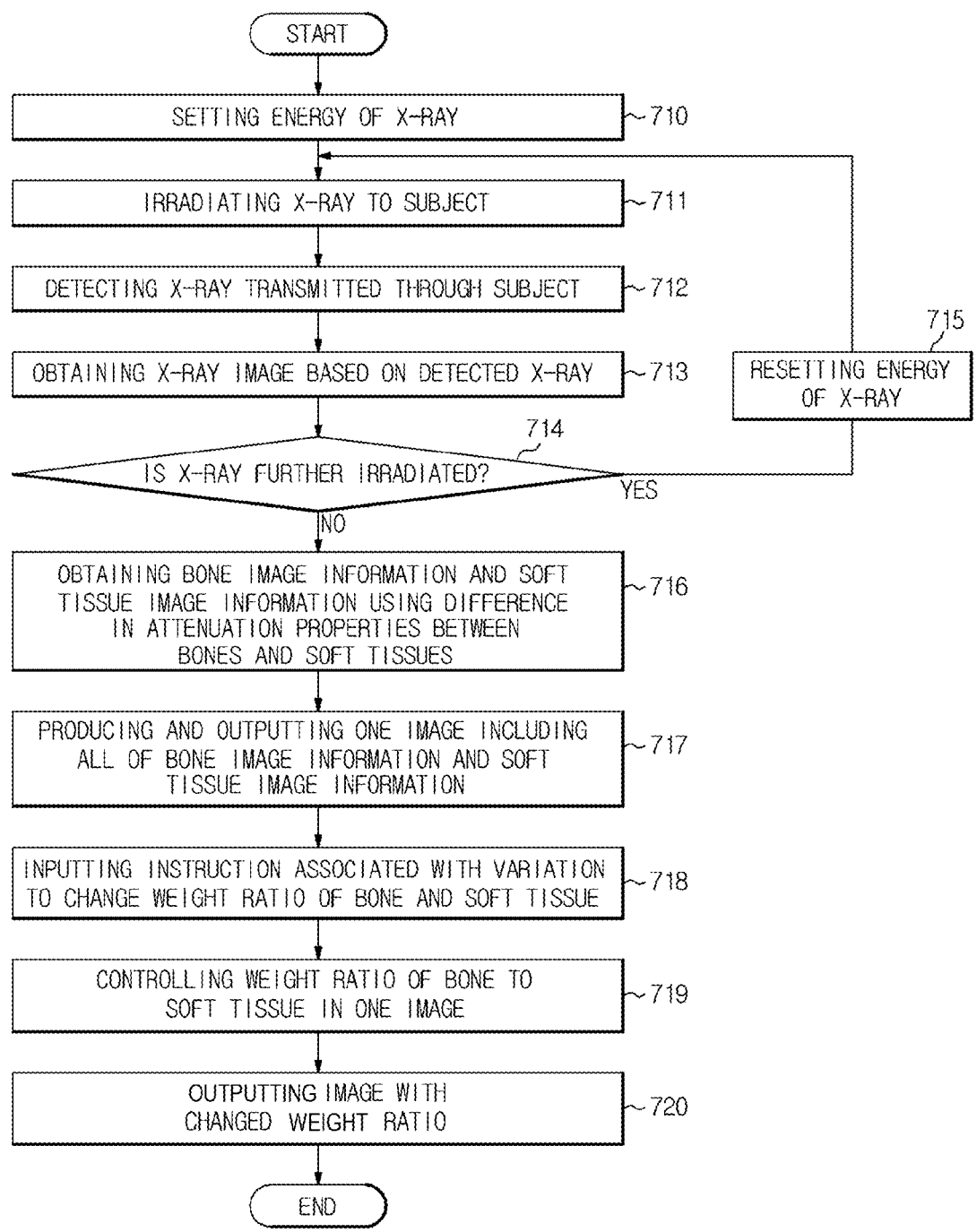
FIG. 23 is a flowchart illustrating a method for controlling an X-ray imaging apparatus according to an exemplary embodiment.

FIG. 23 is a flowchart illustrating a method for controlling an X-ray imaging apparatus according to the exemplary embodiment described with reference to FIG. 15.

The operations 710, 711, 712, 713, 714, 715, 716, and 717 correspond to the operations 610 to 617 described above with reference to FIG. 17 and a detailed description thereof is thus omitted.

When an X-ray image is produced and output, a weight ratio of the bone to soft tissue in one image may be 1:1 or may be changed.

The user inputs instructions to change the weight ratio of the bone and soft tissue, in operation 718. Input of instructions may be carried out using a keyboard, mouse, touch panel, movable member or the like.

The image generator controls a weight ratio of the bone to soft tissue in one image according to the input instruction, in operation 719, and outputs the image having the changed weight ratio through the image output, in operation 730. The output may be carried out by changing a weight ratio of the bone to soft tissue in the output X-ray image.

The methods for obtaining an X-ray image described with reference to FIGS. 17 to 23 are carried out by irradiating an X-ray at different energy levels to obtain images of respective X-rays having different energy levels. However, in any of exemplary embodiments, X-rays having various energies and X-ray images associated therewith may be obtained using PCD by irradiating an X-ray once, as described above with reference to FIG. 16.

As apparent from the foregoing, an exemplary embodiment provides an X-ray imaging apparatus and a method for controlling the same for obtaining an X-ray image of the bones and soft tissues using X-rays having different levels of energy, wherein one image of bones and soft tissues is output to enable a user to confirm conditions of a subject by obtaining only one image and, at the same time, to easily confirm a relation between the bones and soft tissues.

An exemplary embodiment provides an X-ray imaging apparatus and a method for controlling the same wherein one image of bones and soft tissues is output and the bones and soft tissues are represented by different colors or brightness levels to enable a user to easily distinguish the bones from the soft tissues and thereby to improve accuracy and efficiency of diagnosis.

Although a few exemplary embodiments have been shown and described, it would be appreciated by those skilled in the art that changes may be made in the exemplary embodiments without departing from the principles and spirit of the invention, the scope of which is defined in the claims and their equivalents.

What is claimed is:

1. An X-ray imaging apparatus comprising:
    an X-ray source which irradiates an X-ray onto a subject;
    a detector which detects the X-ray transmitted through the subject; and
    a device which obtains an X-ray image data from the X-ray detected by the detector, obtains bone image information and soft tissue image information of the subject, based on the obtained X-ray image data, and produces one image including the bone image information and the soft tissue image information.

2. The X-ray imaging apparatus according to claim 1, wherein the device comprises:
    an image generator which produces the one image including the bone image information and the soft tissue image information; and
    an image output device which outputs the one image produced by the image generator.

3. The X-ray imaging apparatus according to claim 2, wherein the image generator adjusts a brightness of a bone region to be different from a brightness a soft tissue region in the one image.

4. The X-ray imaging apparatus according to claim 2, wherein the device further comprises:
    a color mapper which separately maps the obtained bone image information and the obtained soft tissue image information onto a first color channel and a second color channel having color different from the first color channel.

5. The X-ray imaging apparatus according to claim 4, wherein the image generator produces the one image including the obtained bone image information and the obtained soft tissue image information which have been mapped onto the first and second color channels.

6. The X-ray imaging apparatus according to claim 2, wherein the device further comprises:
    an input device which receives a selection of at least one of a bone and a soft tissue, from a user,
    wherein the image generator further produces another image including only the image information of the bone or the soft tissue selected via the input device.

7. The X-ray imaging apparatus according to claim 3, wherein the device further comprises an input device which receives a selection of at least one of the bone region and the soft tissue region, from a user,
    wherein the image generator adjusts the brightness of a selected one of the bone region or the soft tissue region in the one image to be different from the brightness of a non-selected one of the bone region or the soft tissue region.

8. The X-ray imaging apparatus according to claim 5, wherein the device further comprises:
    an input device which receives a selection of one of the bone image information and the soft tissue image information mapped onto the first and second color channels, from a user,
    wherein the image generator further produces another image including only one of the bone image information or the soft tissue image information selected via the input device.

9. The X-ray imaging apparatus according to claim 5, wherein the device further comprises:
    an input device which receives a selection of one of the bone image information and the soft tissue image information mapped onto the first and second color channels, from a user,
    wherein the image generator further produces the one image including a selected image information and a non-selected image information, and adjusts a brightness of a region of the bone to be different from a brightness of a region of the soft tissue in the one image.

10. The X-ray imaging apparatus according to claim 4, wherein color mapping performed by the color mapper is set or changed by a user.

11. The X-ray imaging apparatus according to claim 2, wherein the device further comprises:
    an input device which receives an instruction to change weights of the bone and the soft tissue in the one image, from a user,
    wherein the image generator controls the weights of the bone and the soft tissue in the one image output by the image output device based on the input instruction.

12. The X-ray imaging apparatus according to claim 1, wherein the device comprises:
    an image output device configured to output the one image as a combination image including both the obtained bone image information and the obtained soft tissue image information.

13. The X-ray imaging apparatus according to claim 12, wherein the device further comprises an input device comprising a user interface comprising a sliding scale configured to receive an instruction to increase or decrease weights of the bone and the soft tissue, respectively, in the one image, and
    the image output device outputs the one image in which an intensity of the obtained bone image information or the obtained soft tissue image information is respectively increased or decreased based on respective input received from the sliding scale.

14. The X-ray imaging apparatus according to claim 1, wherein the detector comprises a flat panel detector.

15. The X-ray imaging apparatus according to claim 1, wherein the X-ray irradiated by the X-ray source has an energy level including a first energy level and a second energy level, and
    the detector is configured to separate the detected X-ray according to the first energy level and the second energy level.

16. The X-ray imaging apparatus according to claim 2, wherein the device further comprises:
    a color mapper configured to separately map the bone image information onto a first color channel or the soft tissue image information onto a second color channel having a color different from that of the first color channel.

17. The X-ray imaging apparatus according to claim 16, wherein at least one of the bone image information and the soft tissue image information of the one image is mapped onto the first color channel or the second color channel.

18. The X-ray imaging apparatus according to claim 2, wherein the device further comprises:
an input device configured to receive an instruction to change weights of the bone or the soft tissue in the one image, from a user,
wherein the image generator is configured to control the weights of the bone or the soft tissue in the one image output by the image output device based on the input instruction.

19. A method for controlling an X-ray imaging apparatus, the method comprising:
irradiating an X-ray onto a subject;
detecting the X-ray transmitted through the subject;
obtaining an X-ray image data from the detected X-ray;
obtaining image information of a bone and a soft tissue of the subject, based on the obtained X-ray image data; and
producing one image including the obtained image information.

20. The method according to claim 19, wherein the producing the one image further comprises adjusting a brightness of a region of the bone to be different from a brightness of a region of the soft tissue in the one image.

21. The method according to claim 19, further comprising:
separately mapping the obtained image information of the bone and the soft tissue, respectively, onto a first color channel and a second color channel having color different from the first color channel.

22. The method according to claim 21, wherein the one image is an image including data of the first and second color channels mapped with the obtained image information.

23. The method according to claim 19, further comprising:
receiving a selection of at least one of the bone and the soft tissue, from a user; and
producing another image including only the image information of the selected bone or the selected soft tissue.

24. The method according to claim 22, further comprising:
receiving a selection of one of the first or second color channels mapped with the obtained image information, from a user; and
producing another image including only the selected color channel.

25. The method according to claim 20, further comprising:
receiving a selection of at least one of the bone and the soft tissue, from a user,
wherein the producing the one image further comprises adjusting a region of a selected one of the bone or the soft tissue to be brighter than a region of a non-selected one of the bone or the soft tissue, in the one image.

26. The method according to claim 22, further comprising:
receiving a selection of one of the first or second color channels mapped with the obtained image information, from a user,
wherein the producing the one image further comprises adjusting a region of a selected one of the first and second color channels to be brighter than a region of a non-selected one of the first and second color channels, in the one image.

27. The method according to claim 19, further comprising:
receiving an instruction to change weights of the bone and the soft tissue in the one image, from a user; and
controlling the weights of the bone and the soft tissue in the output image, depending on the input instruction.

28. A non-transitory computer-readable storage medium storing a program, which when executed by a computer, causes the computer to perform a method comprising:
irradiating an X-ray onto a subject;
detecting the X-ray transmitted through the subject;
obtaining an X-ray image data from the detected X-ray;
obtaining image information of a bone and a soft tissue of the subject, based on the obtained X-ray image data; and
producing one image including the obtained image information.

29. The non-transitory computer-readable storage medium according to claim 28, wherein the producing the one image further comprises adjusting a brightness of a region of the bone to be different from a brightness of a region of the soft tissue.

30. The non-transitory computer-readable storage medium according to claim 28, wherein the method further comprises:
separately mapping the obtained image information of the bone and the soft tissue onto a first color channel and a second color channel having color different from the first color channel.

31. A method for controlling an X-ray imaging apparatus, the method comprising:
generating X-rays having at least two different energy levels different from one another and irradiating the X-rays having the different energy levels onto a subject;
detecting the X-rays transmitted through the subject;
obtaining an X-ray image data from the detected X-rays;
obtaining image information of a bone and a soft tissue of the subject, based on the obtained X-ray image data; and
producing one image including the obtained image information.

32. An X-ray imaging apparatus comprising:
an X-ray source configured to irradiate an X-ray onto a subject; and
a device configured to obtain bone image information and soft tissue image information of the subject, based on the X-ray transmitted through the subject, and produce one image including the bone image information and the soft tissue image information.

33. The X-ray imaging apparatus according to claim 32, wherein the device comprises:
an image generator configured to produce the one image including the bone image information and the soft tissue image information; and
an image output device configured to output the one image produced by the image generator.

34. The X-ray imaging apparatus according to claim 33, wherein the device further comprises:
a color mapper configured to separately map the bone image information onto a first color channel or the soft tissue image information onto a second color channel having a color different from that of the first color channel.

35. The X-ray imaging apparatus according to claim 34, wherein at least one of the bone image information and the soft tissue information of the one image is mapped onto the first color channel or the second color channel.

36. The X-ray imaging apparatus according to claim 33, wherein the device further comprises:
an input device configured to receive an instruction to change weights of the bone or the soft tissue in the one image, from a user,
wherein the image generator is configured to control the weights of the bone or the soft tissue in the one image output by the image output device based on the input instruction.

37. An X-ray imaging apparatus comprising:
an X-ray source configured to irradiate an X-ray onto a subject;

a detector configured to detect the X-ray transmitted through the subject; and a device comprising:

an information acquirer configured to obtain bone image information and soft tissue image information of the subject, based on the detected X-ray;

an image generator configured to produce one image including the bone image information and the soft tissue image information;

an image output device configured to output the one image produced by the image generator; and an input device configured to receive an instruction to change weights of the bone or the soft tissue in the one image, from a user, wherein the image generator is configured to control the weights of the bone or the soft tissue in the one image output by the image output device based on the input instruction.

38. An X-ray imaging apparatus comprising:

an information acquirer configured to obtain bone image information and soft tissue image information of a subject, based on a plurality of X-ray images of the subject corresponding to a plurality of energy levels; and an image generator configured to produce one image including the bone image information and the soft tissue image information.

39. The X-ray imaging apparatus according to claim 38, further comprising:

an image output device configured to output the one image produced by the image generator.

40. The X-ray imaging apparatus according to claim 38, further comprising:

a color mapper configured to separately map the bone image information onto a first color channel or the soft tissue image information onto a second color channel having a color different from that of the first color channel.

41. The X-ray imaging apparatus according to claim 39, further comprising:

an input device configured to receive an instruction to change weights of the bone or the soft tissue in the one image, from a user, wherein the image generator is configured to control the weights of the bone or the soft tissue in the one image output by the image output device based on the input instruction.

42. An X-ray imaging apparatus comprising:

an X-ray source configured to irradiate an X-ray onto a subject;

a detector configured to detect the X-ray transmitted through the subject; and a device configured to obtain X-ray image data from the X-ray detected by the detector, obtain bone image information and soft tissue image information of the subject, based on the obtained X-ray image data, separately map the bone image information onto a first color channel or the soft tissue image information onto a second color channel having a color different from that of the first color channel and produce one image including the bone image information and the soft tissue image information.

\* \* \* \* \*